United States Patent
Carron et al.

(10) Patent No.: US 6,558,956 B1
(45) Date of Patent: May 6, 2003

(54) METHOD AND APPARATUS FOR DETECTION OF A CONTROLLED SUBSTANCE

(75) Inventors: Keith T. Carron, Laramie, WY (US); Robert C. Corcoran, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 0 days.

(21) Appl. No.: 09/446,168

(22) PCT Filed: Jun. 24, 1998

(86) PCT No.: PCT/US98/12974

§ 371 (c)(1),
(2), (4) Date: Dec. 17, 1999

(87) PCT Pub. No.: WO98/59234

PCT Pub. Date: Dec. 30, 1998

Related U.S. Application Data

(60) Provisional application No. 60/050,716, filed on Jun. 24, 1997.

(51) Int. Cl.[7] ............................................... G01N 21/65
(52) U.S. Cl. ..................... 436/86; 356/301; 442/68.1; 442/82.05; 442/82.06; 442/82.09; 442/82.11; 436/91; 436/92; 436/93; 436/96; 436/98; 436/104; 436/107; 436/815; 436/816; 436/901
(58) Field of Search .................... 356/301; 422/68.1, 422/82.05, 82.06, 82.09, 82.11; 436/86, 91–93, 96, 98, 104, 107, 815, 816, 901

(56) References Cited

U.S. PATENT DOCUMENTS

| | | |
|---|---|---|
| 3,062,612 A | 11/1962 | LeBoucher |
| RE30,627 E | 5/1981 | Bagshawe et al. ......... 23/230 R |
| 4,284,553 A | 8/1981 | Brown et al. ............ 260/112 R |
| 4,674,878 A | 6/1987 | Vo-Dinh ..................... 356/301 |

(List continued on next page.)

FOREIGN PATENT DOCUMENTS

WO 98/59234 12/1998

OTHER PUBLICATIONS

J. T. Young et al, J. Adhes. 1994, 44, 119–134.*
Q. Dai et al, J. Adhes. Sci. Technol. 1995, 9, 1465–1474.*
W. H. Reusch "An Introduction to Organic Chemistry" 1997, Holden–Day, Inc.: San Francisco, California, pp. 338–339.*
T.–Y. Li et al, Arch. Biochem. Biophys. 1979, 197, 477–486.*
J. D. Andrade et al, SPIE 1986, 718, 280–285.*
M. Tsen et al, Anal. Chim. Acta 1995, 307, 333–340.*
W. B. Caldwell et al, J. Am. Chem. Soc. 1995, 117, 6071–6082.*
K. L. Morse et al, Life Sci. 1005, 23/24, 1957–1962.*

(List continued on next page.)

*Primary Examiner*—Arlen Soderquist
(74) *Attorney, Agent, or Firm*—Santangelo Law Offices, P.C.

(57) ABSTRACT

Techniques and devices for detecting and analyzing controlled substances and the like are discussed including highly reactive sensor molecules which are coated on a spectroscopic sample surface (4) and which may chemically react with a given analyte to form a covalently bonded adduct with spectral characteristics unique to the new adduct. The techniques provide the basis of a detection system with high sensitivity and high specificity in which the surface can even be washed to remove interfering or nonreactive compounds. The sensor molecules which comprise the coating (8) may have three major components: a central molecular scaffold ("CMS"), a "tether" terminated by a surface attachment group "SAG," and a reactive functional group "RFG" which may be highly reactive towards certain classes of molecules. One or more modifiers or modifier groups "Z" which may serve to increase or decrease the reactivity of the RFG towards target analytes, or to modify the spectral characteristics of the adduct may also be included. Some sensor molecules include diazonium compounds, activated acyls, and nitrosos.

95 Claims, 7 Drawing Sheets

U.S. PATENT DOCUMENTS

| | | | |
|---|---|---|---|
| 4,781,458 A | 11/1988 | Angel et al. ................ | 356/301 |
| 4,802,761 A | 2/1989 | Bowen et al. .............. | 356/301 |
| 4,844,613 A | 7/1989 | Batchelder et al. ......... | 356/318 |
| 4,857,273 A | 8/1989 | Stewart ....................... | 422/68 |
| 4,877,747 A | 10/1989 | Stewart ...................... | 436/525 |
| 4,939,264 A * | 7/1990 | Heiman et al. ............. | 436/537 |
| 5,017,007 A | 5/1991 | Milne et al. ................ | 356/301 |
| 5,023,053 A | 6/1991 | Finlan ..................... | 422/82.05 |
| 5,132,097 A | 7/1992 | Van Deusen et al. .... | 422/82.09 |
| 5,144,030 A * | 9/1992 | Wang et al. .................. | 546/89 |
| 5,255,067 A | 10/1993 | Carrabba et al. ........... | 356/301 |
| 5,262,333 A * | 11/1993 | Heiman et al. ............. | 436/537 |
| 5,266,498 A | 11/1993 | Tacha et al. ................ | 436/525 |
| 5,294,402 A | 3/1994 | Schrepp et al. ............... | 422/57 |
| 5,327,211 A | 7/1994 | Carron et al. ............... | 356/301 |
| 5,376,556 A | 12/1994 | Tarcha et al. ............... | 436/525 |
| 5,400,136 A | 3/1995 | Vo-Dinh ..................... | 356/301 |
| 5,496,700 A | 3/1996 | Ligler et al. ................. | 435/7.1 |
| 5,567,628 A | 10/1996 | Tarcha et al. ............... | 436/525 |
| 5,576,216 A | 11/1996 | Patchornik ................... | 436/86 |
| 5,607,643 A | 3/1997 | Xiaoming et al. ....... | 422/82.05 |
| 5,618,926 A * | 4/1997 | Salamone et al. .......... | 530/403 |
| 5,693,152 A | 12/1997 | Carron ....................... | 148/271 |
| 5,834,224 A | 11/1998 | Ruger et al. .................. | 435/14 |

OTHER PUBLICATIONS

R. de la Torre et al, J. Anal. Toxicol. 1996, 20, 165–170.*

P. C. White et al, Analyst 1996, 121, 835–838.*

K. Aoki et al, Jpn. J. Toxicol. Environ. Health 1997, 43, 285–292.*

C. Gojon et al, Sens. Actuators B 1997, 38–39, 154–162.*

V. Matejec et al, Sens. Actuators B 1997, 38–39, 438–442.*

Albert, B., et al, *Molecular Biology of The Cell*, Second Edition; pp 125–126 and pp 167–168, (1989).

Boyer, J. H.; Canter, F.C., *Alkyl and Aryl Azides*, Chemical Reviews, 54, pp 1–20, (1954).

*Complete Low–Cost Raman Systems, The New Solution™* Series, 7 pages.

Dou, X., et al,*Enzyme Immunoassay Utilizing Surface–Enhanced Raman Scattering of the Enzyme Reaction Product*, Anal. Chem., vol. 69, pp 1492–1495, (1997).

E. Roth and W. Kiefer, 1994 Society for Applied Spectroscopy, *Surface–Enhanced Raman Spectroscopy as a Detection Method in Gas Chromatographgy*, pp 1193–1195.

G.J. Rosasco and E.S. Etz, *The Raman Microprobe: A New Analytical Tool*, Research/Development, Jun. 1977, p. 19 of a total of 17 pages.

Hegarty, A. F. in *The Chemistry of Diazonium and Diazo Groups*, part 2, S. Patai, ed.: John Wiley and Sons: New York, 1978, pp. 511–591.

Ken Mullen and Keith Carron,, *Adsorption of Chlorinated Ethylenes at 1–Octadecanethiol–Modified Silver Surfaces*, 1994 American Chemical Society, pp 478–483.

Machacek, V.; Machackova, O.; Sterba, V., Kinetics and Mechanism of Diazo Coupling. XV. *Coupling Kinetics of Substituted Benzenediazonium Salts with Acetone*, Collection of Czech Chemical Communications, 35, pp 2954–2964, (1970).

Machacek, V.; Machackova, O.; Sterba, V., *Kinetics and Mechanism of Diazo Coupling. XX. Coupling Kinetics of Substituted Benzenediazoniumlons with Substituted—Methylglyoxal Phenylhydrazones*, Collection of Czech Chemical Communications, ibid., 36, 3187–3196, (1971).

Mullen, Ken I.; Carron, Keith T., Surface–Enhanced Raman Spectroscopy with Abrasively Modified Fiber Optic Probes, Analytical Chemistry, vol. 63, No. 19, Oct. 1, 1991, 63, pp 2196–2199, (1991).

Ritchie, C. D.; Saltiel, J. D.; Lewis, E.S., *The Reaction of Diazonium Salts with Nucleophiles. VIII. The Formation of Diazosulfones and the Application of Linear Free Energy Equations to Diazonium Salt Reactions*, Journal of the American Chemical Society, 83, 4601–4605, (1961).

Ritchie, C. D.; Wright, D. J., *Cation–Anion Combination Reactions. IV. Reastions of Aryldiazonium and Cyanide Ions with Hydrooxide Ions in Aqueous Solution*, Journal of the American Chemical Society, 93, 6574–6577, (1971).

Rohr, T. E., et al, *Immunoassay Employing Surface–Enhanced Raman Spectroscopy*, Analytical Biochemistry, vol. 182, pp 388–398, (1989).

S. E. Krahler, *p–Quinone Imine Dyes*, The Chemistry of Synthetic Dyes and Pigments, H. A. Lubs, ed.: Reinhold Publishing, New York, 1955: Chapter 5, pp. 263–266.

Zollinger, H., *Azo Coupling Reactions, Color Chemistry*, VCH Publishers, New York (1991), chapter 7.3, pp 117–127.

Ngeh–Ngwainbi, Foley, J., Kuan, P. H., Guilbault, G. G.; "Parathion Antibodies on piezoelectric Crystals", J. Am. Chem. Soc., 1986, 108,18, 5444–5447.

Suleiman, A. A., Guilbault, G. G.; "Recent Developments in Piezoelectric Immunosensors", Analyst, 1994, 119, 2279–2282.

Suleiman, A. A., Guilbault, G. Gl; "Piezoelectric (PZ) Immunosensors and Their Applications", Analytical Letters, 1991, 24, 1283–1291.

Attili, B. S., Suleman, A. A.; "A Piezoelectric Immunosensor for the Detection of Cocaine", Microchemical Journal, 54, 1996, 174–179.

Rouhi, A.; "Land Mines: Horrors Begging for Solutions", C&EN, 1997, Mar. 10, 14–22.

Katerkamp, A., Bolsmann, P., Niggemann, M., Pellmann, M., Cammann, K.; "Micro–Chemical Sensors Based On Fiber–Optic Excitation of Surface Plasmons", Mikrochim. Acta., 1995, 119, 63–72.

Ehler, T. T., Noe, L. J.; "Surface Plasmon Studies of Thin Silver/Gold Bimetallic Films", Langmuir, 1995, 11, 4177–4179 John M. Bowen, Lewis J. Noe, B. Patrick Sullivan.

Ehler, T. T., Malmberg, N., Noe, L. J.; "Characterization of Self–Assembled Alkanethiol Monolayers on Silver and Gold Using Surface Plasmon Spectroscopy", J. Phys. Chem., 1997, 101, 1268–1272.

Whelan, J. P., Kusterbeck, A. W., Wemhoff, G. A., Bredehorst, R., Ligler, F. S.; "Continuous–Flow Immunosensor for Detection of Explosives", Anal. Chem. 1993, 65, 3561–3565.

Scott Paulson, Kevin Morris and B. Patrick Sullivan; A General Preparative Route to Self–assembled Monolayer Surfaces of Polypyridine Ligands and their Metal Complexes, Department of Chemistry, University of Wyoming, Laramie, WY 82071–3838, USA, pp. 1615–1617.

Ligler, Frances S.; Anderson, George P.; Davidson, Peggy T.; Foch, J. Richard J.; Ives, Jeffrey T.; King, Keeley D.; Page, Greg; Stenger, David A.; Whelan, James P.; "Remote Sensing Using an Airborne Biosensor," Environmental science & technology; Aug. 15, 1998 v 32 n 16; p: 2461, American Chemical Spociety.

J. B. Heyns et al., "SERS Study of the Interaction of Alkali Metal Ions with Thiol–Derivatized Dibenzo–18–Crown–6", Analytical Chemistry May 1994, vol. 66, No. 9, pp. 1572–1574.

S. M. Angel et al., "Development of a Drug Assay Using Surface–Enhanced Raman Spectroscopy", SPIE 1990, vol. 1201, pp. 469–473.

R. J. Lacey, "Some Advanced in the Use of Raman Spectroscopy in Security Screening Applications", IEE Conference Publication, Apr. 1997, vol. 437, pp. 10–12.

P. R. Carey et al., "Resonance Raman Labels: A submolecular Probe for Interactions in Biochemical and Biological Systems", Accounts of Chemical Research 1978, vol. 11, pp. 122–128.

E. L. Torres et al., "Trace Determination of Nitrogen–Containing Drugs by Surface Enhanced Raman Scattering Spectroscopy on Silver Colloids", Analytical Chemistry, Jul. 1987, vol. 59, No. 13, pp. 1626–1632.

K. I. Mullen et al., "Trace Detection of Ionic Species eith Surface Enhanced Raman Spectroscopy", Spectroscopy, Jun. 1992, vol. 7, No. 5, pp. 24–31.

L. M. Cabalin et al., "Surface–Enhanced Raman Spectrometry for Detection in Liquid Chromoatography Using a Windowless Flow Cell", Talanta 1993, vol. 40, No. 11, pp. 1741–1747.

J. M. E. Storey et al., Applications of Surface–Enhanced Raman Scattering (SERS) to Chemical Detection, Spectroscopy, Mar./Apr. 1995, vol. 10, No. 3, pp. 20–25.

E. A. Wachter et al., "Hybrid Substrate for Real–Time SERS–Based Chemmical Sensors", Applied Spectroscopy, 1995, vol. 49, No. 2, pp. 193–199.

O. Zaborsky, "Immobilized Enzymes", 1973, pp. 5–48.

R. A. Messing et al., "Covalent Coupling of Alkaline Bacillus Subtilis Protease to Controlled–Pore Silllica with New Simplified Coupling Technique", Chemical Abstracts, vol. 82, Mar. 3, 1975, abstract 53464d (Mol. Cell. Biochem. 1974, vol. 4, No. 3, pp. 217–220).

N. Yu. Abramov et al., "Sythesis and Spectral Luminescent Characteristics of Acylhydrazones Immobilized on the Surface of Carboxymethyl Cellose and Aerosil", Journal of Analytical Chemistry 1994, vol. 40, No. 7, pp. 636–639.

Y. C. Liu et al., Reactions of Organic Monolayers on Carbon Surfaces Observed with Unenhanced Raman Spectroscopy, Journal of the American Chemical Society, 1995, vol. 117, No. 45, pp. 11254–11259.

B. E. Baker et al., "Solution–Based Assembly of Metal Surfaces by Combinatorial Methods", Journal of the American Chemical Society , 1996, vol. 118, No. 36, pp. 8821–8722.

Y. C. Liu et al., "Raman Spectroscopic Determination of the Structure and Orientation of Organic Monolayers Chemisorbed on Carbon Electrode Surfaces", Analytical Chemistry, Jun. 01, 1997, vol. 69, No. 11, pp. 2091–2097.

* cited by examiner

METHOD AND APPARATUS FOR DETECTION OF A CONTROLLED SUBSTANCE

This application is the U.S. National Stage of International Application No. PCT/US98/12974, filed Jun. 24, 1998, which claims the benefit of U.S. Provisional Application No. 60/050,716, filed Jun. 24, 1997, each hereby incorporated by reference.

I. TECHNICAL FIELD

Generally this invention relates to the field of detecting the use of controlled substances such as illicit drugs and the like. More specifically, the invention involves the field of Raman spectroscopy to accomplishing detection and the sub-field known as Surface Enhanced Raman Scattering. In a less focused sense, this invention relates to a method of detecting substances through the use of a coated surface and spectroscopic techniques. The invention also covers the use of a new coating with a tethered reactive species that chemically binds to an analyte. Through this new technique, the analyte is then spectroscopically analyzed as part of a new chemical species which is the reaction product of the analyte and the reactive species.

II. BACKGROUND ART

The field of sensing controlled substances is an area which has evolved primarily for the public good. As practically everyone knows, drug and alcohol abuse are significant problems for society. In fact, in 1998 the United Nations conducted an international anti-drug conference involving over one hundred nations which are facing this societal challenge. As society attempts to address this problem it has turned to increasingly sophisticated technical analysis to counter the abuser's attempt to hide either the controlled substance or its use. Naturally, the principles of analytical chemistry have been relied upon for their ability to not only detect but to discriminate the presence of a controlled substance in minute amounts. Unfortunately at its present state, the field of detecting controlled substances still has difficulty in both sensing and discriminating the existence of some substances as well as in avoiding false positive indications. This invention provides a solution that greatly expands the techniques and accuracy available for a variety of substances. It also provides a framework under which practical advantages can now be achieved. These advantages range from the seemingly simple ability to provide a single sensor for a variety of drugs as well as the ability to now be able to discriminate between controlled substances and some chemically similar uncontrolled substances. This latter aspect can be significant because in a variety of applications such as Olympic drug testing and the like, it has become difficult to accurately sense and distinguish the difference between certain substances which are legally available for use and those which are truly illegal substances. In a broader sense, the invention also provides an expansion to the principles of analytical chemistry since it may be applied in other areas as well.

The field of analytical chemistry dates back at least to Pliny the Elder (AD 23–79) who first described the use of an extract from gallnuts that turns black in the presence of iron sulfate. This allowed him to determine if copper sulfate was contaminated with iron sulfate. This simple concept of chemical analysis has grown into analytical chemistry which is one of the four disciplines of modern chemistry. Analytical chemistry encompasses a variety of fields such as clinical chemistry, environmental chemistry, geochemistry, and forensic chemistry. The techniques of analytical chemistry have grown from the simple wet chemical analysis discovered by Pliny the Elder to very sophisticated instrumental methods. Early analytical chemistry relied on visual observation of color changes or the precipitation of a compound to quantitate materials. This meant that the sensitivity was often limited to the visual acuity of the chemist. Instruments have largely replaced these visual techniques, since it is possible to electronically detect changes in light intensity and wavelength with vastly superior sensitivity.

The electronic detection of changes in light intensity and its separation into different wavelengths is the basis of the field of analytical spectroscopy. This is an area in which some type of analyte, namely, some substance or chemical which is desired to be studied, is exposed to some wavelength of energy. This wavelength may be a singular wavelength such as a laser often provides, or it may be many different wavelengths. To provide the information desired, the analyte then causes some type of change in that incident energy and thus results in some type of change in intensity of at least one wavelength of energy which is characteristic of the analyte. Thus the wavelength of energy to which the analyte is exposed and the changed signal resulting usually vary. Naturally, the incident energy may be present in a variety of forms as those aware of the wave-particle duality may easily understand. Essentially, however, all that spectroscopy involves is an incident wavelength which is somehow affected by an analyte to result in a changed signal. This signal may be a singular wavelength or may be a broad spectrum of wavelengths of emission or adsorption. Thus, "spectroscopy" as intended here is not intended to be limited to only some type of slit-based instrument, but rather is intended to fully encompass the areas of analytical chemistry in which changes in wavelengths of energy are studied to gain information with regards to an analyte. Conversely, it should be understood that other fields or areas of study which do not involve changed wavelengths have not been viewed as particularly relevant to this field. For example, the areas of chromatography and the like which act to separate substances, immunoassays which transiently bind substances for nonspectroscopic purposes, and the like, have not been viewed as particularly relevant to the fields in which this invention relates.

As mentioned earlier, the field of sensing controlled substances faces a variety of limitations. These range from imperfect discrimination (such as in the Olympic drug testing scenarios) to practical challenges such as the need to have different tests for different substances. When considering spectroscopic techniques, great improvement has occurred through the introduction of a technique known as Raman spectroscopy. Raman spectroscopy was discovered by Sir Chandrasekhara Venkata Raman in the early 1900s who found that different chemicals sometimes caused unique scattering of an incident wavelength of energy. Since the scattering was largely unique to each chemical, the analysis of the specific scattering thus provided information from which specific chemical detection and identification could be achieved. Unfortunately, limits remained even with the introduction of Raman spectroscopy.

In 1976, a new spectroscopic technique was discovered that is sensitive to interfaces. This technique has been coined Surface Enhanced Raman Scattering (SERS). SERS tends to give large enhancements of Raman scattering in the presence of certain prepared metallic surfaces. The SERS technique has been applied to a variety of problems—not only those associated with analytical chemistry—and more recently has been the subject of several publications and patents for analytical chemistry. This technique generally involved some type of attachment of an analyte to a metal surface or to a coating on a metal surface such as gold or silver.

Even in the broader area of general analytical chemistry, initially, the coatings were not tethered to the metal surface. In U.S. Pat. No. 5,326,211 relating to analytical chemistry in general, Carron and Mullen showed that it was possible to coat a surface with a dye that had complexed with a metal ion to serve as a metal ion detector. Again in the broader field of analytical chemistry, Angel was awarded an early patent, U.S. Pat. No. 4,781,458 for the determination of analytes adsorbed directly to metals surface or partitioned onto a coating. Even more recently some publications by Carron and U.S. Pat. No. 5,327,211 disclosed the use of SERS with coatings that contain thiols to tether the coatings to a silver surface. That disclosure specifically addresses the use of SERS coatings on a fiber optic to allow for remote sensing. Carron, et. al, has demonstrated that the coatings mimic separation science coatings and also serve to stabilize the SERS substrate to give it longevity. The coatings can also provide an internal standard that allows one to use relative intensities to determine a calibration that can be used to find the concentration of the analyte.

The general techniques of SERS has been well established and is discussed to some degree not only in the above general analytical chemistry references, but also in a variety of references ranging from text books to additional patents such as U.S. Pat. No. 5,693,152 to Carron, U.S. Pat. No. 5,255,067 to Carrabba, and U.S. Pat. Nos. 5,266,498, 5,376,556, and 5,567,628 to Tarcha in the immunoassay field. To the extent necessary, each of these references is hereby incorporated by reference to provide additional understandings as they relate to the Raman and SERS techniques generally.

One of the perspectives that has evolved to those focusing on these techniques has been a perspective that suggests that it may be more appropriate to avoid changing any structures or spectral characteristics of an analyte during its spectroscopic analysis. This perspective seems rooted in the understanding that, naturally, if one wants to detect the analyte itself, it would be better not to alter the analyte or controlled substance. Thus, the coatings developed to date for analytical applications of SERS have been coatings that weakly interact with the analyte to produce a reversible measurement of the analyte concentration. These include alkylthiols that mimic the nonpolar coatings used in reverse phase HPLC, pH and metal sensitive coatings that mimic ion chromatography, and oxide coatings that mimic normal phase chromatography.

By weakly interacting with the analyte to produce a measurable spectrum, the goal of seeing only the analyte spectrum had been satisfied. As a result, the techniques of Raman spectro-scopy and specifically that of Surface Enhanced Raman Scattering, had to some degree been viewed as limited since the surfaces typically used in SERS have been the relatively unreactive substances of gold and silver. Since these substances can cause the desired weak interactions in only a few situations, these techniques, while powerful for certain analytes, had not been as greatly exploited as possible in the field of detection of controlled substances. In essence, since a goal was that the surface itself created some sort of weak link with the controlled substance, and since not many controlled substances would establish an appropriate link with the typically required gold or silver surfaces, these techniques were often not viewed as particularly appropriate to the field of detection and analysis of controlled substances or specific substances and the like. The techniques were also viewed as somewhat limited themselves because it seemed that they could really only be used for those specific types of analytes that happened to bond appropriately to the required surface. Although eventually different sample surfaces did exist for certain different analytes, generally the selections were so limited that the techniques were perhaps underutilized.

One example of efforts to alter the surface involved in the SERS technique is disclosed in U.S. Pat. No. 5,693,152 to Carron, one of the present inventors. In that patent, Carron disclosed a technique to modify the surface enhanced Raman scattering (SERS) detector by applying a stabilizing coating on the SERS surface. The coating applied would reproduce or mimic the specific separation procedure being utilized thus this method could be used universally for all types of analytes and separation methods. Similar to the invention disclosed in a patent by Carrabba et al (U.S. Pat. No. 5,255,067), a roughened surface substrate was used to improve SERS detection efficiency in gas chromatography. However, although the coating disclosed in '152 patent can locally increase the analyte concentration and improve linking affinity between the coating and the analyte, the attachment of these analytes to the coatings are still through weaker linking mechanisms, primarily by means of adsorption or other weak forces.

Similarly, other, perhaps unrelated fields have seen efforts to alter binding sites in the immunoassay area. As mentioned earlier, the use of SERS technology for immunoassays has been disclosed by Tarcha et al. In U.S. Pat. Nos. 5,266,498, 5,376,556, and 5,567,628. In their disclosures the authors designed a Raman active reporter which is bound to a specific binding member. However, this is not only an immunoassay method, it involves attachment of an analyte to a binding member through weaker techniques and thus even though it is in an unrelated area, seems to show the pervasiveness of the perspectives and attitudes of those involved in Raman spectroscopy.

In the focused field of detecting controlled substances, however, the problems seem even more acute. Those involved in sensing controlled substances (and other, even uncontrolled substances) have faced problems with the discrimination abilities between substances. The problems for professional athletes who may have taken some type cold medicine prior to their participation in the Olympic games has been highly popularized. From one perspective this problem may be viewed as a simple byproduct of the inability of the analytical techniques to adequately discriminate between a legal cold medicine and the remnants as a result of the use of an illegal drug.

Another problem which is the fact that it is desirable to sense controlled substances in extremely low concentrations. Again, the seemingly irresolute requirement that the analyte or controlled substance only weakly binds with the spectroscopic surface has made it challenging to sense such low concentrations because the equilibrium values are often such that the analyte would desorb from the surface and not permit a sufficient build up to facilitate high quality detection. Further, a problem has existed in instances in which it was desired to not only detect but to quantify the presence of either some controlled substance or more generally an analyte, over a broad ranges of concentrations. In those instances in which such spectroscopic techniques were found to apply, it was often the case that the ranges over which a specific sensor could be used made it practically difficult to achieve the technique.

Furthermore, because there are a great variety of controlled substances, one of the problems has been in the ability to use the specific spectroscopic technique to sense not only one specific type of controlled substance but to sense a great variety of substances. Not only have there existed limitations on which specific substances interact appropriately with which specific sensors, but there have existed seemingly fundamental limitations such that certain substances could not be analyzed through Raman techniques. Naturally, while many of these problems are particularly acute in the focused field of sensing controlled substances, it can be easily understood that these problems also applied to more general applications of spectroscopic techniques as well.

One way in which the apparent requirement of a weak interaction has resulted in a difficulty is the practical fact that interfering substances are often present. While it would be desirable to remove these interfering substances, the weak interaction has made it more difficult to remove the interfering substances without also removing some analyte as well. Even the improved SERS coating disclosed in U.S. Pat. No. 5,693,152 highlights that this problem continued unsolved. Essentially, the problem was that while such a SERS coating could specifically adsorb material from the matrix, there were no ways of washing the surface to remove the interferences either unavoidably or practically present in the matrix. Furthermore, since the interaction of the analyte with the surface was often viewed as necessarily reversible, it was implied that the interaction needed to be weak. Physically, this often meant that only a small amount of the analyte tended to interact with the surface or could be detected in a given instance.

Thus, in the field of sensing controlled substances, there has been a long felt but unsatisfied need for a detection technique which could be applied to a great number of controlled substances and which could also provide a higher degree of discrimination between such substances especially those which were not considered illegal. Even though those skilled in the field of sensing controlled substances appreciated this desire, they seemed not to have fully appreciated the nature of the problem in that their perspective was driven by certain preconceptions which actually limited their ability to solve the problems with which they were faced. To some degree their substantial attempts failed to fill the need either because their field did not require the basic physical understanding of the phenomenon or they simply assumed that existing techniques could not be adapted to their unique needs. For this reason, it appears that those skilled in the art to some degree actually taught away from the direction in which the present inventors went.

As related to the broader field of analytical chemistry in general, it appears that similar perspectives also apply. For instance, while those in the field of analytical chemistry in general well appreciated that it was desirable to apply sensitive techniques such as Raman spectroscopy and the SERS techniques to a greater variety of substances, their apparent tendency was to approach the problems from the perspective of seeing primarily the analyte as opposed to some altered by-product. Again, while they had expended substantial efforts to expand the applicability of the techniques, their focus toward physisorption perhaps showed that they did not fully appreciate the nature of the problem. They seemed thus to teach away from the direction in which the present inventors went pursuing avenues that in hindsight might be viewed as based on misperceptions to some degree. Not only were these misperceptions fostered by the initial desire to sense an unaltered analyte, but they also were fostered by attitudes which seemed to suggest that reversible and remote sensing arrangements were required for some practical reason. Thus, to some degree the present invention might even be characterized as unexpected in the sense that it proposes techniques and substances which, prior to this invention, were not just deemed suboptimal but rather were viewed as contrary to the goals typically considered and the results typically desired.

In addition to the aspect of applying analytical techniques to a greater variety of substances, those generally applying the techniques had long felt a need for an ability to apply those techniques to greater ranges of concentrations and to greater varieties of chemicals during one analysis event. Even though a desire existed, they may not have fully appreciated that the problem and solution lay not in sample preparation or non-spectroscopic techniques, but in adjustments to the analytical technique itself or to the specific sensors involved in the analytical technique. Efforts focussed in a direction different from those of the present inventors may have been due to the fact that those involved did not to some degree fully appreciate that sensor chemistry could offer the needed advances and simplifications.

III. DISCLOSURE OF THE INVENTION

To address these and other problems, the present invention involves techniques and devices which offer improved spectroscopic analysis capabilities. As applied to the field of sensing controlled substances, the invention involves the creation of a unique surface coating such as a diazonium or other type of coating which interacts with the substance in a wholly different manner. Rather than forming the weak interactions that were previously viewed as perhaps required, the invention creates a whole different type of interaction, namely a full reaction such as in the formation of a covalent bond to produce an entirely different species, termed here in adduct. Since in most instances the formation of this covalent bond is irreversible, the rate of loss of the controlled substance or other analyte from the surface will be approximately zero. As a result, washing or other steps to remove interference substances can now be accomplished. Thus, as a result, the invention offers a greatly expanded Surface Enhanced Raman Scattering technique through which coatings may be altered as appropriate for specific substances and through which expanded ranges and sensitivities can now be accomplished. Thus the detection of substances which are controlled, substances of a medical nature, or simply some new types of analytes are now possible. In its approach, the invention breaks with what may have been preconceptions and utilizes a substance, such as diazonium, which is highly reactive with the controlled substance or other analyte at issue. Thus the diazonium and the like may interact to permanently bond or perhaps covalently bond with the analyte as opposed to the more typical weak chemisorption or physisorption. Through this reaction the diazonium may be viewed as an advantage rather than a hindrance in that an actual adduct is created and rather than studying the analyte in isolation the resulting adduct is studied.

In a more basic form, the invention includes a method of detecting molecules by chemically binding them to a surface and then using a surface-sensitive detection method. This is a significant improvement over the existing method of attracting molecules to a surface through weak forces. The new technique increases the sensitivity of detection by forming a strong bond between the analyte and the surface coating. The equilibrium between surface analytes (e.g. detectable analytes) and solution analytes (e.g. not detectable since not captured by the surface) may be characterized by an equilibrium constant. In one sense, the equilibrium constant describes the number of species at the surface relative to solution. In another sense, it describes the rate at which molecules go on the surface relative to the rate at which they come off. The present invention describes a method of forcing the off rate to be essentially zero and to thereby greatly increase the number of species on the surface (e.g. the detectable species). This is one form of sensitivity improvement. A second method of improvement comes from the ability to wash the surface after the analyte has bonded to the surface. In many cases, the sensitivity of an analytical method has been limited due to the presence of large interfering backgrounds. This background arose from species in the solution with the analyte that gave rise to a signal that was similar to that of the analyte. These interfering species can now be removed with this invention since the analyte is bound to the surface and the interfering species can be easily washed off without affecting the analyte. (This, of course may, not work for every analyte possible.) A third method of improvement comes from the ability to distinguish between different analyte types. Because the adduct formed through formation of a covalent bond is a new and unique chemical species, it will likely have unique spectroscopic characteristics. Since different analytes will form different adducts, they may be distinguished from each other on the basis of the differing spectra, thus decreasing the likelihood of mistaken identification.

In the field of sensing controlled substances, it is thus an object of the invention to provide techniques and devices which may be applied to a greater variety of controlled substances and which may be applied to all substances with a higher degree of sensitivity, with greater ability to discriminate, and even with the possibility of confirmational systems to be automatically in place to avoid false indications. In keeping with these objects, it is a goal of the invention to offer a system which is controlled to a lesser degree by the equilibrium constants of a reaction and which even offers situations where the equilibrium constant is essentially zero. Similarly, a goal is to provide a system in which interfering substances and the like can be removed without concern of removing or somehow reducing the signatures available as a result of the controlled substance itself. A further goal is for a system which permanently binds the controlled substance to the sensor surface and thus can be analyzed at any location or any time without a high degree of concern of degradation of the signal.

A more broadly stated goal for the invention in the field of sensing controlled substances is that of providing techniques which can be designed for specific chemicals in specific situations. Thus a goal is to provide a system which can be optimized through chemical design for either specific substances or for specific ranges and broader substances in one analytical event.

An object as it relates to the broader field of analytical chemistry in general, as well as in the field of detecting controlled substances, is to provide a system in which internal standards can permit the monitoring and compensation for alterations in the illumination source as well as to provide techniques in which coatings rather than the surfaces themselves can be used in a variety of detection techniques. Thus, the invention could be used with a large variety of analytical techniques, known to those in the art. Optical techniques such as Raman, fluorescence, or absorption spectroscopy could be used for detection. Mechanical detection would also be possible with sensitive mass sensors. Raman scattering may prove to be one of the most desirable detection methods. Surface Enhanced Raman Scattering (SERS) provides large enhancements in the Raman scattering from molecules near certain metal surfaces. The invention thus involves methods of anchoring our molecule specific probes to this type of surface. Moreover, while the invention contains a fairly high specificity for specific classes of molecules it may not need to be truly specific to a single molecule. SERS, of course, is a truly molecular-specific detection method. This means that a complex mixture of species in a reactive class of compounds could react with the surface and SERS could differentiate and quantitate between the various species.

The use of SERS also provides a substantial improvement over many techniques through the use of an internal standard. The internal standard furnished by this invention can be the portion of the surface tether that is unchanged by the reaction of the reactive functional group (RFG) with the analyte. This portion of the surface coating may give rise to a SERS signal that can be monitored simultaneously with that of the analyte. A simple ratio of the two signals or a more sophisticated multi variate analysis can be used to give a detection method that is independent of source intensity fluctuations or variations in the detection throughput. This creates the possibility for more simplified and less expensive instrument design as well as design for rugged, maintenance free use.

IV. BRIEF DESCRIPTION OF DRAWINGS

FIG. 1 shows spectra of a prototype coating, 4-amino phenyldisulfide, and its reactivity toward phenols. A) A SERS spectrum of 4-amino phenyldisulfide. The disulfide bond has broken and the surface species is 4-amino thiophenylate. B) A SERS spectrum of the coating used in Figure A after treatment to make it into a diazonium salt. C) A SERS spectrum of the coating in Figure B after exposure to phenol. The Raman features around 1512 cm−1 are indicative of the azo functionality. The shows that the coating reacted with phenol to make an azo compound.

FIG. 2 is an example of the components that might be present in the instrument required to read the results of the current invention. The input may be for a sample entry, the source may be some sort of light source, the sample compartment may be where the measurement is made after reacting with the coating, the optics may be used to transfer and modify the signal prior to detection, the detector may be a transducer that converts an optical signal into an electrical signal that could be read by a computer, and the output may be a computer that converts the electrical signal from detector and performs analysis on the data to produce a result. The result may be a simple detection, a quantitation, or even a full identification of the amount of analyte in the sample.

FIG. 3 is a schematic showing prior art and the current invention. Bottom) the prior art shows molecules attracted to coatings through weak intermolecular forces. Top) the current invention shows bonding of an analyte to the coating. Here the analyte may be localized at the coating through an intramolecular force (e.g. a chemical bond) that strongly holds onto the analyte.

V. BEST MODE OF CARRYING OUT THE INVENTION

As can be easily understood, the basic concepts of the present invention may be embodied in a variety of ways. It involves both analysis techniques as well as devices to accomplish the appropriate analysis. In this application, the analysis techniques are disclosed as well as various devices described and as steps which are inherent to utilization. In addition, while some devices are disclosed, it should be understood that these not only accomplish certain methods but also can be varied in a number of ways. Importantly, as to all of the foregoing, all of these facets should be understood to be encompassed by this disclosure.

Figure 1A:
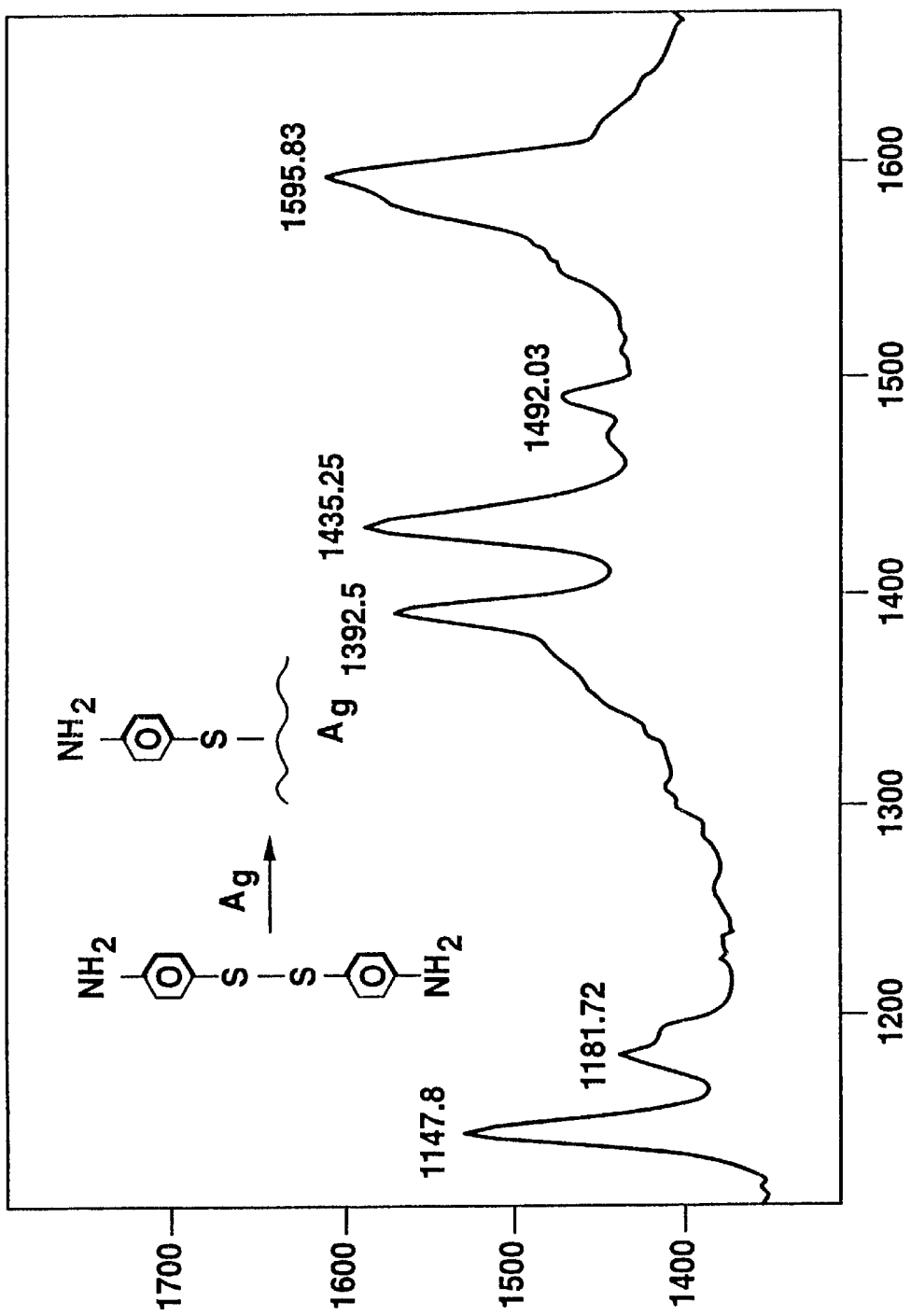
Figure 1B:
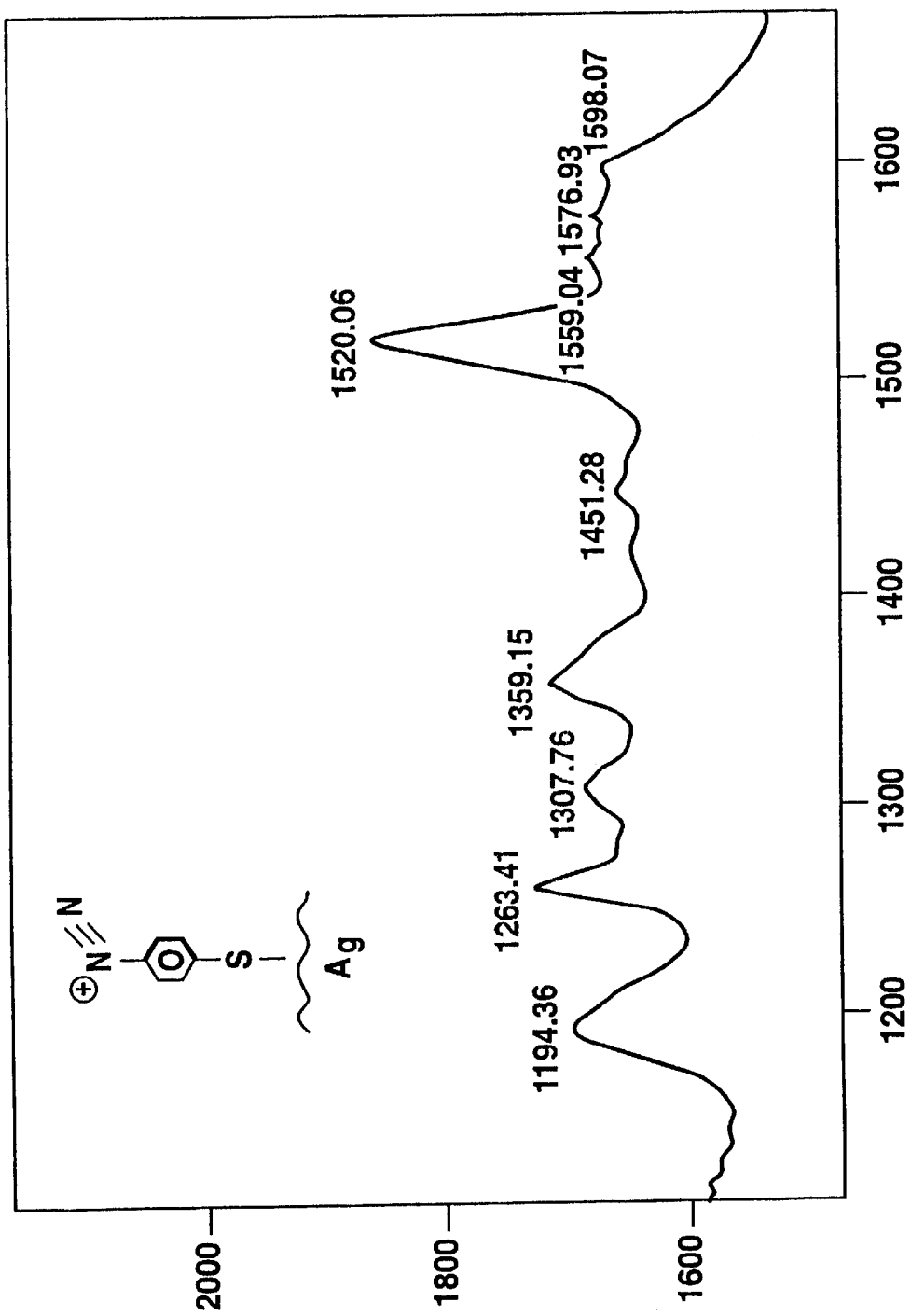
Figure 1C:
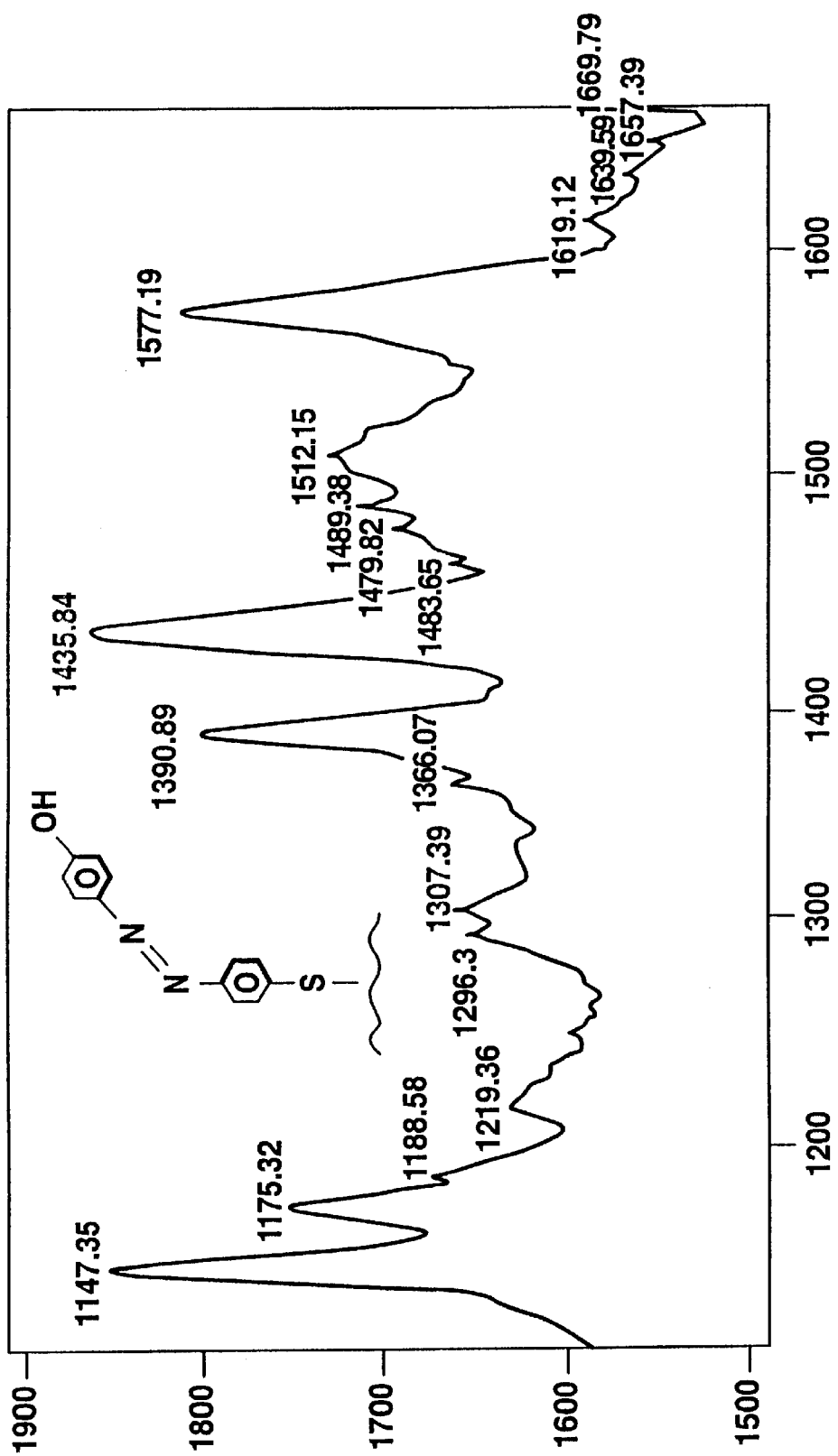
Figure 2:
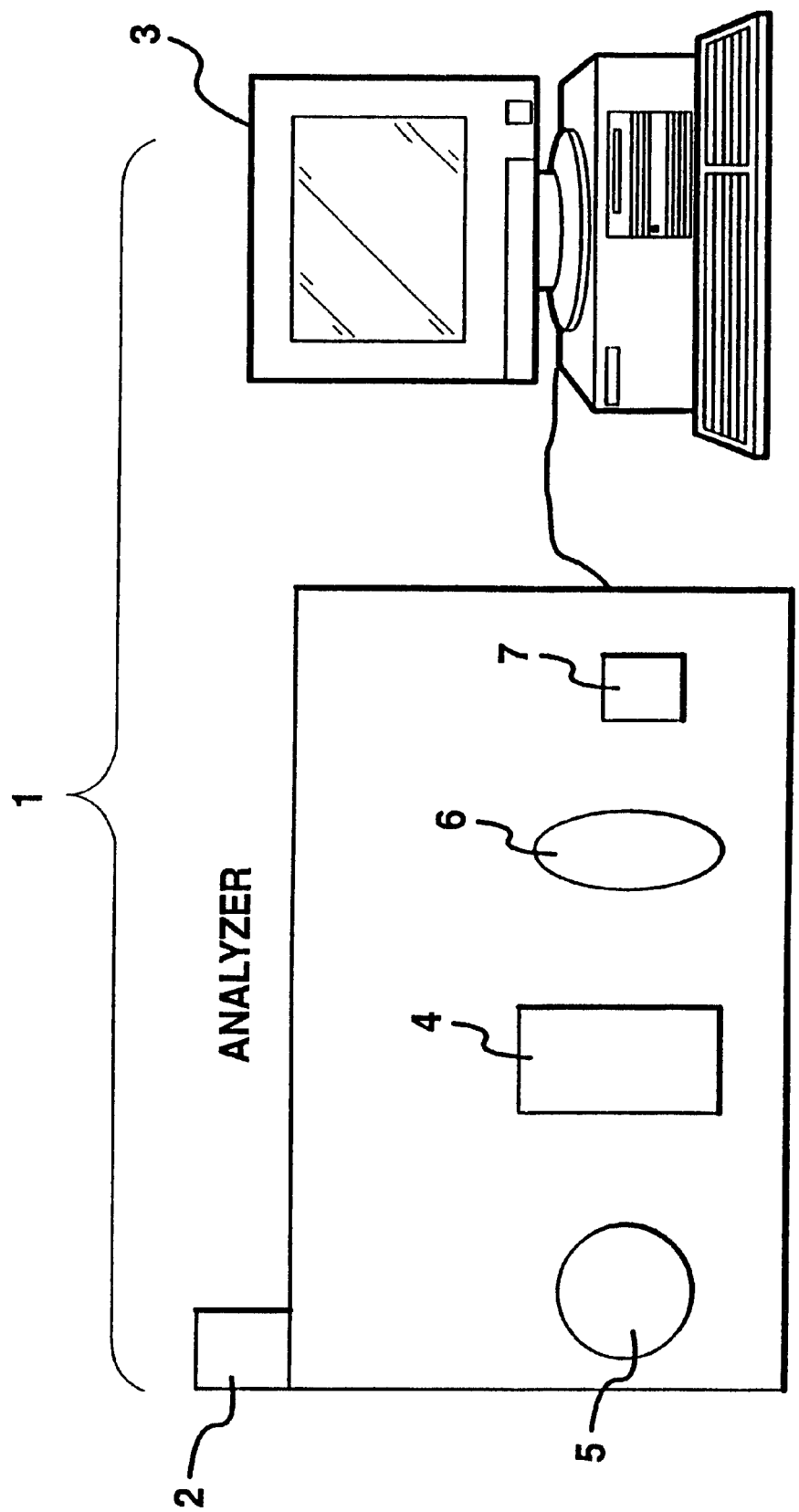
Figure 3A:
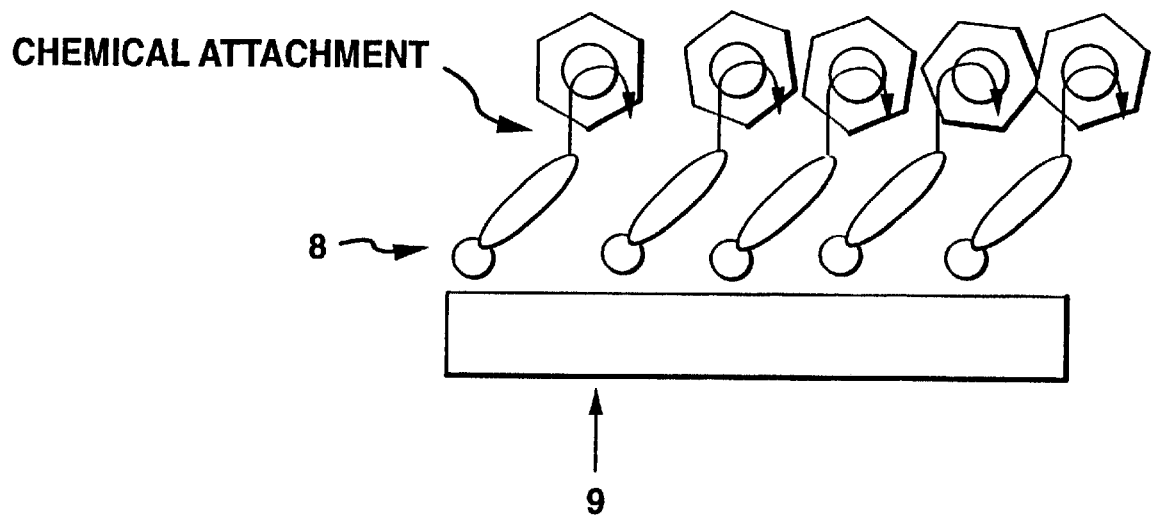
Figure 3B:
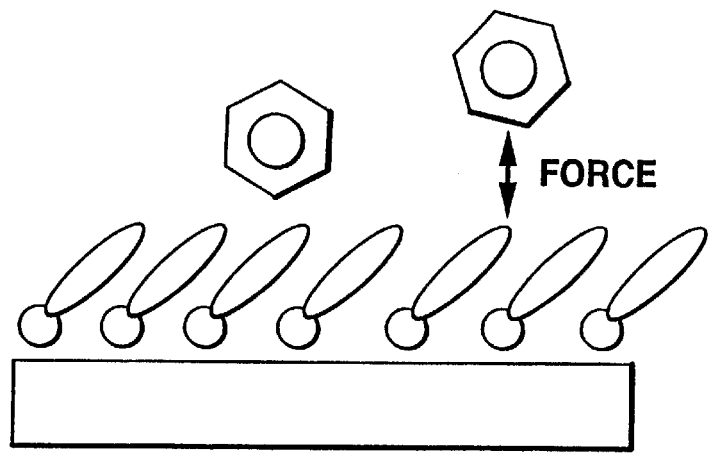

The general spectroscopic technique can be easily understood from reference to FIG. 2. FIG. 2 shows an analyzer (1) which has some type of input (2) and results in some type of output (3). Either by providing the analyte or controlled substance itself or by providing an input where some type of sample surface or sample (4) can be provided to the analyzer (1), input (2) facilitates sample (4) to be provided within analyzer (1). Since the focus is upon analysis through spectroscopy, analyzer (1) as well as the various components are configured for spectroscopic analysis. Either within or external to analyzer (1), some type of source (5) may provide one or more wavelengths of energy to which a spectroscopic sample (4) is exposed. The source (5) may be a laser or some other type of highly regulated light source. It may also be some type of broad spectrum source. Typically, the source (5) has been highly regulated to provide a constant output. In keeping with one of the aspects of the present invention, less expensive sources might now be used. In general, however, the spectroscopic sample (4) may be provided so that the source (5) can be exposed to it in a manner that at least one incident wavelength of energy can impinge upon the sample (4). In this way source (5)—which may be virtually any type of illumination device—can illuminate the sample (4). Since most spectrographic analysis which is of interest in the present invention involves the analyte being on some type of surface, sample (4) may configured as a spectroscopic sample surface. As such the sample has the appropriate characteristics for a particular spectroscopic technique. In the situation of Surface Enhanced Raman Scattering, the spectroscopic sample surface may have such characteristics as those skilled in the chemical arts readily understand so that the spectroscopic sample surface can interact and provide an appropriate Raman scattering or surface enhanced Raman scattering as the case may be. The spectroscopic sample surface may include on it some type of event location which may either be the entire surface or singular locations (such as wells) so that many different analytes or sensors can be utilized.

In keeping with the present invention, the spectroscopic sample surface may be adapted so as to retain the analyte through some type of attachment link. While in the prior art, this attachment link may have include primarily weak interactions, in the present invention a significant difference may be provided so that the attachment link creates either a permanent link or perhaps a covalent link in some manner. Regardless of the specific type of link, the attachment link is designed so that at least at one spectroscopic sample location the analyte or controlled substance can be linked in some manner which can be spectroscopically sensed, that is, in a manner so that an appropriate spectral change exists as a result of the analyte's presence. A significant departure by the present invention with respect to the teachings of the prior art is that this link may retain the analyte—or at least some component chemical or other aspect of the analyte—through formation of a covalent bond, or stronger interaction.

When the source (5) provides at least one wavelength of energy, the incident wavelength of energy can be affected in some manner at least in part by the analyte as it is retained on the spectroscopic sample surface. This broad possibility, namely, the fact that it merely affects the spectroscopic signal means that the signal can either be a totally new signal (such as that of an adduct), or it can simply alter the signal in some indirect manner by the presence of the analyte. The alteration then results in a spectroscopic signal which is typically changed emission or adsorption wavelength(s) of energy so as to produce a signature which can be analyzed and determined uniquely as a result of the presence of the particular analyte desired. The sample (4) can either have on it, or be itself, some type of sensor molecule which interacts with the analyte. The changed wavelength or wavelengths may then be further focused or conditioned by optics (6) so that some type of detector (7) can be positioned to receive the changed wavelength or perhaps the spectroscopic signal. This signal can then be provided for some type of analysis.

The analysis may consist of a computer determination through comparison software or some other determination, all as is well known, to gain information with respect to the analyte or controlled substance. Thus, the analyzer (1) acts so as to spectroscopically analyze the signal. This analysis may be as simple as comparisons to known spectra or other data which may be stored in a computer or other such device.

As mentioned, it may be desirable to have a spectroscopic sample surface. As those skilled in the chemical arts readily understand, for Raman spectroscopy this spectroscopic sample surface may actually be a Raman spectroscopic sample surface or a Raman surface, namely, a type of surface which provides the appropriate interactions to achieve the Raman scattering phenom-enon. Similarly, for Surface Enhanced Raman Scattering spectroscopy this spectroscopic sample surface may actually be a Surface Enhanced Raman Scattering spectroscopic sample surface, namely, a type of surface which provides the appropriate interactions to achieve the Surface Enhanced Raman Scattering phenomenon. Likewise, the illumination source may be a specific Raman illumination source, namely, the type of source appropriate for Raman Spectroscopy so that Raman illumination is exposed to the sample (4) to produce Raman scattering or a Surface Enhanced Raman Scattering illumination source. It should also be understood that the surface, while typically a somewhat planar solid, may also include suspended particulates and the like so long as an appropriate Raman or other sensor molecule type is included to permit the interactions desired.

As mentioned earlier, the focus on spectroscopic analysis differentiates the invention from other separation types of techniques. Such techniques may include chromatography or other aspects which, although often incidentally used, are fundamentally different from the field of spectroscopic analysis. Chromatographic techniques often simply separate materials on the basis of their interaction with a surface. Here, early chromatography used paper, activated charcoal, or alumina to separate polar materials from a nonpolar solvent phase. This allowed the analytical chemist to remove polar interference from a nonpolar analyte or to sequester a polar analyte onto a stationary matrix and flush away nonpolar interferences. As the chromatographic field has advanced, it is possible to separate materials based on smaller and smaller differences in affinity for the solid stationary phase. More recently, the field of liquid chromatography has improved through the use of affinity coatings. The coatings allow one to chemically modify the solid stationary phase such that it possess affinities different from the uncoated material. A classical example is the coating of silica which is a very polar surface with an alkylsilane to produce a very nonpolar surface. This makes it possible to partition nonpolar materials onto the stationary phase and to have a polar solvent phase (mobile phase). This form of chromatography is called reverse phase chromatography. The realization that coatings could be used to modify the chemical properties of the solid phase led to the development of charged coatings. These are used for yet another form of chromatography called ion chromatography. This form of chromatography utilizes Coulombic attraction and polarization forces to separate charged species from a non-charged mobile phase. All of the above described chromatographic methods use an interfacial forces for separation. While they may be incidentally used in the preparation of samples for spectroscopic methods, they are not themselves a spectroscopic analysis technique. Similarly, affinity chromatography which is often used to isolate or purify enzymes, may involve transient bonding to substrates, however, again, this technique is primarily a separation technique and is not designed for spectroscopic analysis. The transient bonding is of necessity nonpermanent as it is simply an intermediate step of enzyme activity and is designed to be released.

Although the prior discussion with regards to spectroscopic techniques focused upon the utilization of SERS and Raman technology, it should be understood that a variety of detections systems could be employed with the present invention to determine the concentration or characteristics of the analyte. At present it simply appears that the most attractive is Surface Enhanced Raman Spectroscopy (SERS) because of the tremendous increase in Raman signal intensity associated with localizing a molecule near a silver, copper, or other appropriate metal surface. SERS is also attractive due to the high information content associated with Raman spectroscopy, which assays the transitions between vibrational states of a molecule. Infrared (IR) spectroscopy, which also detects vibrational transitions in molecules, is also a good candidate for a detection system. Because the sensor coating and subsequent adduct coating are both surface bound, the most probable application of IR spectroscopy would be in the context of direct-, or indirect-reflectance Fourier transform infrared spectroscopy (FTIR), in which the lower sensitivity of the technique could be compensated by the multiple acquisition and subsequent analysis of spectra. Other optical techniques which might be applied to measuring concentrations of the surface bound species are fluorescence (or photorescence) spectroscopy, or the measurement of fluorescence (or phosphorescence) lifetimes. Non-optical techniques which could be utilized for these measurements could include electrochemical methods (e.g., voltametric or amperometric methods). In the simplest cases (e.g., those in which only a single analyte is likely to be encountered), any other method (spectroscopic or nonspectroscopic) which can be used to characterize the presence of a species at a surface could also be utilized, provided that it could distinguish between the sensor coating and the adduct coating. More demanding applications (i.e., more than one possible analyte) would probably require a technique which could distinguish between the sensor coating and each of the possible adduct coatings.

As disclosed, the coating may consist of a variety chemical classes. Carbon containing groups such as those having some carbon atom in their structure and even non-protein groups of coatings could be used as the reactive coating. As contemplated in one of the preferred embodiments, a diazonium compound or some derivative of that compound could be used as a sensor coating. The diazonium compound may also include a diazonium salt sensor coating. Any diazonium compound sensor coating could be selected in situations in which the particular analytes involved would react appropriately with the diazonium compound sensor coating in order to provide the desired spectrum. Thus, a controlled substance which reacted appropriately would be considered a diazonium-specific controlled substance. In this manner at least some chemical of the diazonium-specific controlled substance would interact with the analyte-reactive coating (8). Some chemicals which represent both controlled substances and appear to be appropriate as a diazonium-specific controlled substance include codeine, heroin, psylocibin, tetrahydrocannabinol and morphine.

Some other specific coatings in keeping with this aspect of the present invention may include activated acyl compounds and their associated acyl-specific controlled substances or analytes. The substances may include not only those mentioned earlier, but also some alcohols, amphetamines, or methamphetamines. Nitroso-sensor coatings may also be used with nitroso-specific analytes as is mentioned later.

As discussed in more detail later, any of the coatings may be placed on the desired surface through techniques easily understood and may thus be used to sense the appropriate substance. This substance may range from general analytes to the controlled substance application mentioned earlier to medical applications as well. In that latter instance, blood substances, namely, those being blood itself or coming from or derived from blood products may be used for detection of either controlled substances or medically important information such as bilirubin or the like. In an analysis, even finger printed or complex spectral characteristics could be provided or used within computer or other capabilities so that individualized determinations might be made. Other applications beyond those mentioned range from mining to environmental applications. Naturally many of these substances would beconsidered controlled substances—that is, they are regulated in some way, be it due to illegal drug use, environmental concerns, or for other reasons.

As mentioned earlier, the linking between the analyte and the coating on the surface of the sample (4), may be selected so as to achieve not merely permanent bonding of the coating to the surface, but, significantly, permanent bonding of the analyte to the coating. Unlike the weak interactions considered appropriate in the prior art, this latter permanent bonding can include links which are merely retained to a significant degree, links which might be truly nonremovable in ordinary use, or even some type of intermediate level of linking. The bonding may include, of course, a covalent bonding such as those skilled in the chemical arts readily understand to be highly permanent or such as may even create a new molecular species. Such a species, namely, the combination of the analyte or controlled substance and the coating can be an adduct or even a covalently bonded adduct. In this embodiment even if a new species (or more importantly spectral signature) is created, the invention recognizes that the original spectral characteristics of the analyte need not be necessarily retained, but rather the spectral characteristics of the adduct may be adequate. Thus an adduct of any kind whether permanent or not, may to some degree present a significant difference over the prior art. Thus, by selecting a coating which is adapted to form a covalent bond with a particular analyte, the original signature of the analyte may be lost, however, the new signature—that of the covalently bonded adduct might now be present. In creating an adduct the spectroscopic signal present may now be very different and may not even be an analyte signal but rather an adduct-specific signal which is produced by the treated surface.

A coating as described above may be specifically created through the use of some sort of reactive functional group which would itself be adapted to form the desired adduct. As is mentioned later, an interesting aspect is that through this technique even slight variations in the reactive functional group of the coating can give very different spectral signals. For instance, simply relocating the functional group on a scaffolding or creating different types of bonds can be used to alter the spectral characteristics and yield a very different spectrum for different analytes or different circumstances.

By including the possibility of creating an adduct as opposed to weakly linking the analyte to the surface, a situation where the equilibrium constant for locating the analyte or adduct at the surface essentially at infinity can be created.

As mentioned earlier, one of the advantages of utilizing permanent or perhaps covalent bonding of the analyte or controlled substance to the spectroscopic sample surface (4) is that once these bonds have been created, they may not be easily removed or broken. Thus it may now be possible for some analytes to wash the surface with a liquid either to remove excess analyte, to stop the continued creation of the bonding of the analyte over a period of time, or to remove interfering substances. With respect to stopping the citation of additional bonding, a greater degree of accuracy may now be possible in that the sample surface prior to being presented to the analyzer (1) maybe washed at a specific time to completely stop any continued creation of the covalent bond. This might also have the added benefit (or independent benefit) of simultaneously removing any interfering substances which can be washed away. Similarly, it is now possible to utilize this washing technique to remove my excess analyte. Again, this may or may not occur simultaneously or may occur independently from the steps of stopping the creation of the covalent banding of the analyte to the coating or the stop of removing interfering substances.

In yet another embodiment of the present invention, the coating may be designed to present an internal standard. By internal standard it is meant that the coating would separately present an unaltered signal which could be sensed to yield information regarding the real time status of the source (5) so that variation in the illumination or detection functions could be factored into the analysis and compensated for without a need for a more expensive laser or other illumination source (5). This internal standard could be a lower or even separate portion of the coating itself. It could also be from a tether group. As such it could present an internal standard which was co-located with the adduct or co-located with the chemical reaction event location (9) so that a singular illumination process could achieve the signal of both a spectrum of the adduct as well as a spectrum for the internal standard. Examples of such an internal standard could include a carbon chain structure, aromatic ring, non-reactive chromophore, a nitro group, a sulfonyl, a non-carbon structure, or other such items as those skilled in the chemical arts would readily recognize. Such an internal standard could be specifically included in the design of the coating itself.

Figure 4:
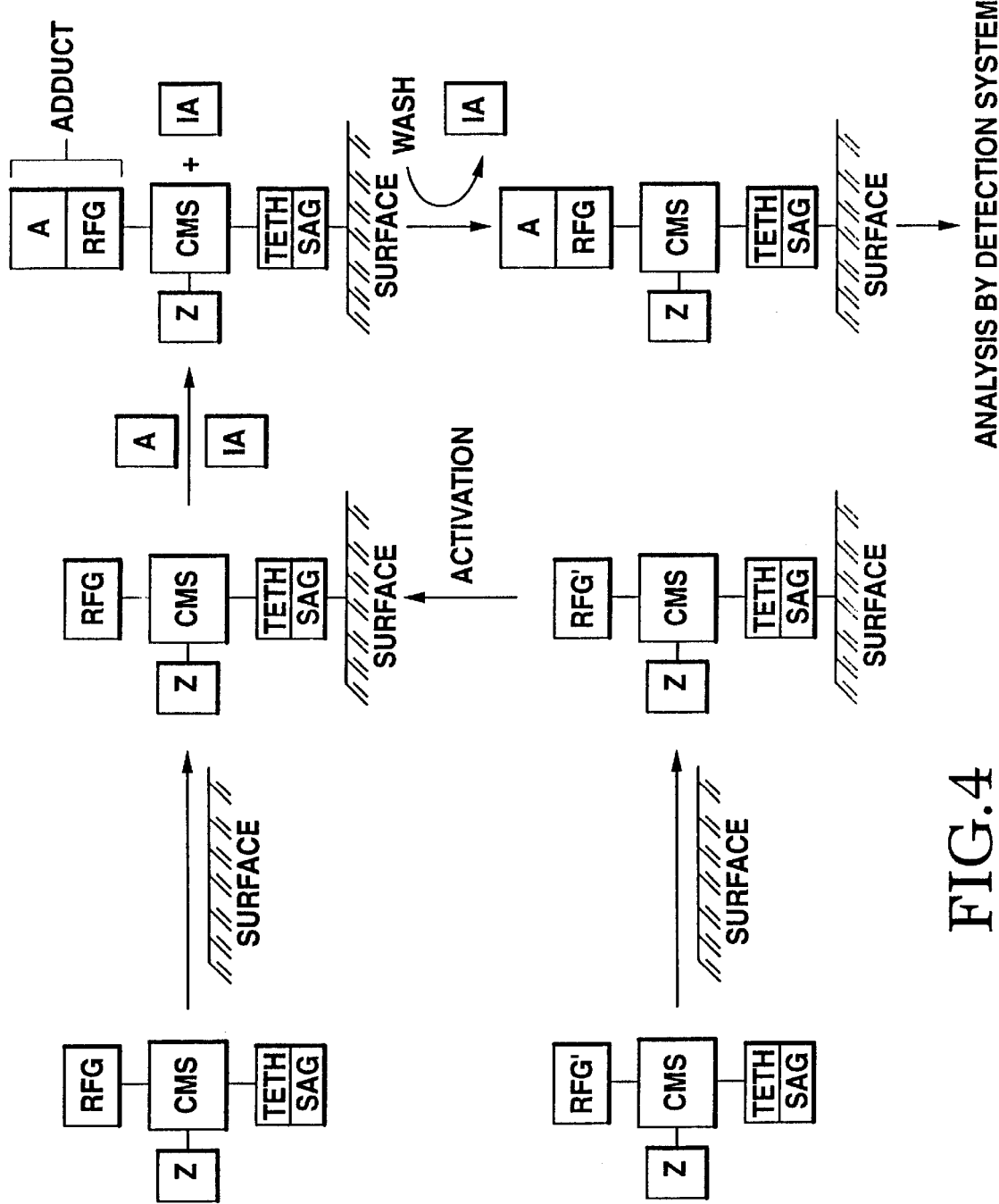
FIG. 4 is a schematic representation of how the detection system may work on a molecular basis, and includes a depiction of a sensor molecule (and some subunits), its attachment to a surface, and its subsequent reaction with an analyte.

The construction of the analyte reactive coating (8) may be achieved in a variety of ways depending on the specifics of the application. One type of design is illustrated diagrammatically in FIG. 4. As shown, a sensor molecule possessing a tether (TETH) could be terminated by a surface attachment group (SAG), a reactive functional group (RFG) and possibly even one or more modifier group(s)(Z). These could be placed on a suitable surface to give the sensor coating. In one of the other embodiments, a precursor molecule having a tether, perhaps a modifier(s) Z, and a RFG-precursor (RFG) may be used to coat a suitable surface. By including a precursor arrangement, the coating might be designed so that in a subsequent step, the RFG' could be transformed to the RFG to yield a fully reactive sensor coating.

In use, the sensor coating could be exposed to the analyte (A). This analyte may be contained within a solid, ligand or gas under conditions which might allow a chemical reaction to take place between the sensor molecules and the analyte. After an optional rinse of the new adduct coating to remove possibly interfering substances or interfering analytes (IA) which do not react, the adduct coating could then be assayed by an appropriate spectroscopic technique to quantify the amount of adduct and/or remaining sensor coating present. Aspects of each of these steps are discussed in detail below.

As discussed above, fine sensor molecule may incorporate a tether, a reactive functional group (or its precursor), and in some instances, a modifier group. All of these groups may be attached to a central molecular scaffolding (CMS).

Since the surface attachment group is designed to hold the coating to the surface, the choice of SAG would likely depends on the surface involved, as well as on the functionality present in the sensor molecule (see below for a discussion of the latter issue). In each instance the surface attachment group, namely, the portion of the molecule which would serve to link atoms in the sensor molecule to the surface could be chosen based upon the type of substrate or surface which is desired to be used. The following discusses a variety of such surface materials; naturally others could be used and in such instances, the SAG would likely be varied as those skilled in the chemical arts would readily understand.

Metal surfaces. Likely metal surfaces include silver, gold, copper and mercury. A particularly appropriate SAG for these surfaces appears to be the thiol group RSH (or RS—) or some derivative of the thiol group such as RCOSM, $RCOS_2M$. ROCOSM, RSCOSM, $RSCS_2M$, $ROP(S)_m$ $(O)_{3-m}M_2$, $RSP(S)_m(O)_3-M_2$, RSSR', RSSSR', RSNR'R", in which R=RFG-Ar-spacer-, M=H or metal ion, and R',R"= alkyl or aryl or H. Other SAG's which might be appropriate are the polar groups $RSO_3M$, $RSO_2M$, $ROSO_3M$, $ROSO_2M$, $RCO_2M$, $ROCO_2M$, $RNR'CO_2M$, $ROP(O)O_2M_2$, $RP(O)O_2M_2$.

Silica, alumina, or florasil surfaces. In addition to the polar group listed for metal surface above, polar SAG's likely appropriate for attachment to these surfaces include RR'R"N, RR'R"R'"N+, and the corresponding phosphine and phosphonium salts in which P replaces N. Other SAG's include $RSiX_3$ (X=leaving group such as halide, inorganic ester, and R, R', R", M defined as for the metal surfaces above), and $RSi(OR')_3$.

Ion exchange resins. Any of the negatively charged SAG's listed under the metal surfaces section above (is., RCOSM, $RCOS_2M$, ROCOSM, RSCOSM, $RSCS_2M$, $ROP(S)_m(O)_{3-m}M_2$, $RSP(S)_m(O)_3$-mM2, $RSO_3M$, $RSO_2M$, $RSO_2M$, $ROSO_3M$, $ROSO_2M$, $RCO_2M$, $ROCO_2M$, $RNR'CO_2M$, $ROP(O)O_2M_2$, $RP(O)O_2M_2$) could be loaded outo an anion exchange resin. Amine, ammonium, or phosphonium salts could be loaded onto cation exchange resins. While coatings of this type would be particularly appropriate for use with analyte solutions not containing potentially competing ions, it may still be possible to utilize these systems for ion containing solutions, since many of the SAG's listed above have particularly high affinity for ion exchange resins, and because appropriate tether design could hinder the exchange rate with undesirable ions.

Plastics. Any of a number of functionalized polymers could be modified with an appropriate SAG. For example, chloromethylation of a polystyrene based plastic could be followed by reaction with RSM, ROM, or RNR'R". Alkyl acrylate or alkylmethacrylate polymers could be subjected to ester exchange with ROH, or aminolysis with RNR'H. It may also be possible to adhere a hydrophobic tether group to a hydrophobic plastic through simple hydrophobic attraction.

Cellulose. An example of this class of surfaces is filter paper. This could be modified by any type of activated carbonyl compound (e.g. RCOX, RNCO, R and X defined as in the metals and silica sections above). Modification of specialized cellulosic material (e.g., cyclodextrins) offers the possibility of unique selectivities towards certain analyte classes.

Coating Methods. There a number of possibilities to create the coating. While many of these are easily understood by those of ordinary skill in the chemical arts, two general approaches may be noteworthy in the formation of a sensor coating: application of RFG-Ar-tether-SAG to give the sensor coating directly, or application of RFG'-Ar-tether-SAG, in which RFG is a group which must be transformed to the desired RFG in a subsequent activation step. The advantages of the first approach are at least two-fold. The prior activation/formation of the RFG should be straightforward, since the reactions leading to it should generally be standard solution phase chemistry. In addition, this approach should typically yield the sensor coating directly. There are, however, potential disadvantages of this approach for some classes of senor coatings and/or SAG's. These disadvantages include the possibility that the sensor coating may not have a long term stability (e.g., due to reaction with adventitious water, oxygen, light), and the possibility that a particular combination of RFG and SAG may not be chemically compatible, or that the RFG may not be compatible with the surface during the coating process (due to the geometry of attachment of the sensor molecule and tether, it could be possible that one could have RFG's which could react with a surface in the process of coating, but could not react once attached to the surface). While it is likely that the potential problem of sensor coating stability could be solved simply by appropriate protective measures (e.g., a dissolvable overcoating, or the use of otherwise hermetically sealed surfaces), the problem of SAG/RFG incompatibility may require the second approach, in which the RFG is formed only after surface coating. In addition to avoiding the problem of functional group incompatibility, this approach may be desirable from the standpoint of sensor coating stability. In practice, a stable pre-sensor coating could be prepared, stored for some indefinite period of time, and then the RFG' converted to the RFG by activation immediately prior to exposure to the analyte. A potential drawback to this approach is the possibility that the desired RFG activation might not occur efficiently on a surface. In some cases, the feasibility of this approach might even need to be determined on a case by case basis. Other approaches may be appropriate depending on market place and other considerations and should be relatively easily designed once the basic principles are understood.

Again, it should be understood that each of the above examples represent merely come choices available depending upon the particular surfaces or other aspects involved in a particular application. Variations should be understood as encompassed within this disclosure since with the basic teachings those of ordinary skill in the chemical arts would be able to achieve variations in any of the components mentioned without undo experimentation.

Attached either directly to the surface attachment group or through same type of tether, may be a central molecular scaffolding. The Central Molecular Scaffolding may serve to physically hold the various components of the sensor molecule in place. It may also play a role in the analysis of the adduct coating. This could be particularly true in the case of spectroscopic techniques which rely on fluorescence, or which require detection at long wavelengths, for which polycyclic aromatic scaffoldings might be particularly well suited. If the modifier Z is to have a direct influence on the reactivity of the RFG, or upon the spectroscopic characteristics of the adduct coating, it might preferably be desirable to have a direct electronic "connection" between Z and the scaffolding, and between the scaffolding and the RFG (and subsequently the analyte portion of the adduct). Once again, this might suggest a central scaffolding which might likely be a monocyclic or polycyclic aromatic (or heteroaromatic) ring. For sensor coatings which primarily act by ensuring the propinquity of target analyte to the surface, it may not be useful to have the electronic connection discussed above. For these system. It may be possible (though not necessary) to employ non-aromatic scaffoldings. In general, however, examples of some central molecular scaffolding groups may include similar types of rings as mentioned earlier with regard to the surface attachment group, namely, the establishment of the monocyclic aromatic ring, a polycyclic aromatic ring, a heteroaromatic ring, or a non-aromatic scaffolding as well.

As mentioned earlier, one of the advantages of an embodiment of this invention is the possibility of removing undesired substances which might have spectral characteristics which interfere with analysis of the target analyte. This may be accomplished by washing the surface layer subsequent to reaction, thus removing the unreacted, interfering substances. From the above description, it may be gathered that this general approach to analyte specificity and enhanced signal-to-noise is not expected to be limited to a specific type of surface, though certain of the spectroscopic methods used for final analysis may require specialized substrates (e.g., silver, gold or copper for use with SERS).

As previously discussed, the surface attachment group may be linked to the central molecular scaffolding through some type of tether. The tethering group attached to the sensor molecule may simply be zero to many carbon or non-carbon atoms in a chain (or incorporating a ring) terminated by a SAG which is appropriate for attachment to the chosen surface. Alternatively, the tether may incorporate a nonreacting chromophore of some sort (e.g., some type of aromatic ring). Such incorporation could allow for the possibility of using the tether chromophore as an internal standard for quantification of the spectroscopic changes on going from the sensor coating to the sensor adduct coating. Tethering chains incorporating aromatic or long-chain aliphatic carbon chains (or perfluorinated carbon chains) also may prove to be advantageous from the standpoint of stability of the sensor coating, since the hydrophobicity of these groups could tend to protect the surface attachment points from the solvent and dissolved solutes. In the ease of detection systems designed for use with nonpolar solvents (e.g., one of the activated acyl based sensor molecules), a polar, nonreacting tether could be utilized. Examples of this type of tether would likely be amide based (e.g., a polypeptide, possibly terminated with cysteine), though other polar tethers could also be employed (e.g., based on sulfonates or sulfoxides). A tether design which would be especially effective in masking a surface from an organic solvent would be one of the type RFG—Ar—$(CH_2)_n$—N+ $R_2(CH_2)_m$—SAG Y—(Y—=counterion), since the ionic interface could effectively preclude migration of nonpolar molecules.

Functionally, an important aspect of the coating may be the inclusion of same type of reactive functional group, namely, a group of atoms which acts in such a fashion as to react with the analyte and link the analyte to the coating. The coating itself may thus be adapted to be attached to the analyte of desire. This attachment may occur through a covalent bond, the mere creation of an adduct, some type of permanent link, or otherwise. Because of the importance of this structural feature of the sensor molecule, and because of the differences in analyte specificity which result from difference in the nature of the RFG, its location and the like, the various classes of RFG's are discussed with some specificity below. General examples of reactive functional groups which can be used include not only the diazonium groups, azo species, and nitrous, but also activated acyl sensors as well as non-protein molecules.

Diazonium. The diazonium group is probably the most interesting and promising of the RFO's due to its high reactivity towards certain classes of molecules, as well as the nature of the adduct it can form with these molecules. While the high reactivity of diazonium salts is well known, and is responsible for their utility in the preparation of diverse functional derivatives of aromatic rings, these ions are not indiscriminately reactive. Thus, proper choice of reaction conditions for their formation leads to diazonium salts which can be kept for long periods in solutions and subsequently reacted with an added reagent, or even isolated and stored for long periods of time prior to redissolution and reaction. One of the characteristic reactions of diazonium salts is the addition of a nucleophile (Nuc) to the terminal nitrogen of the $ArN_2$+ group to give azo species Ar—N═N—Nuc. As a consequence of the high degree of conjugation and polarizability of these azo species, they are in many cases dyes, and appear especially well suited by virtue of wavelength of maximum absorption ($\lambda$max) and/or extinction coefficient ($\epsilon$) to detection by any of a number of techniques. Alternative pathways for nucleophiles involve substitution (directly, or indirectly through the intermediacy of an azo species) of the N2+group to give a new aromatic species. Though the new species often may not have as desirable spectral characteristics as the azo type products, the replacement of the unique N2+ chromophore by a different group typically is distinct. One of the classical reactions of diazonium salts, that can result in the formation of aryl chlorides and aryl bromides, follows a radical pathway demanding the presence of copper (or other metal) salts, and may be unlikely to occur except under specially designed conditions.

Nitroso. Aryl nitroso compounds are expected to share many of the same desirable features of diazonium salts in terms of their reactivity with selected classes of potential analytes, and in terms of the desirable spectral characteristics of the resulting adducts. Aryl nitroso compounds may react with amines to form azo compounds (Z—Ar—NO+ RNH2 gives Z—Ar—N═N—R) which, as indicated above, sometimes form the basis of many dyestuffs. If an electron rich phenol or aromatic amine is employed, then nitroso compounds may react to form quionimine, or quinodiimine type structures. These reactions can be exemplified by the formation of the dye gallocyanine (from gallic acid and p-nitrosodimethylaniline) and Nile Blue A from 1-naphthylamine.

Activated Acyl Sensors. This class of RFG or sensor molecules comprise compounds having a reactive acyl type carbon. In addition to compounds in which the reactive carbon is in the oxidation state of a carboxylic acid (e.g., acid chlorides, imino esters, iminium esters, etc.), this class of compounds should be understood to include compounds in which the reactive carbon is in the oxidation state of carbon dioxide (e.g., carbonyl halides (ROCCO), isocyanates, diimides, etc.). Examples are illustrated in FIG. 5, along with the structures of the adducts expected upon reaction with alcohols and amines (RXH, X═O and NH or NR', respectively). All of these compounds are expected to be highly reactive towards water, and thus it is likely that sensors based on this type of reactive functional group will be of greatest utility for directly assaying non-aqueous and non-alcoholic solutions. Exceptions to this generalization may, of course, occur if the analyte of interest is of sufficiently great reactivity (and sufficiently high concentration) that it may compete with water/alcohol for the RFG. An alternative to directly assaying an aqueous sample might involve extraction of the analytes of interest from an aqueous solution into an organic solvent, followed by exposure of the extract to the sensor coating. Similar considerations as those discussed above for the preparation of the sensor coating may apply here as well. Although direct formation of a surface from a molecule incorporating the desired RFG may have some practical benefits, depending on the specific identities of the RFG and SAG, it may be necessary or advantageous to prepare a coating having from a molecule which has a group RFG' that may be unreactive, but which may be transformed to the RFG after formation of the coated surface.

Both the diazonium and activated acyl sensor coatings might be used for the detection of controlled substances and the like. Particularly the activated acyls may also be used for alcohols and amines as well. The nitroso coatings though likely not as applicable for drug sensing also may offer specific chemicals for which they are appropriate. In general, the sensor coatings may include a wide variety of general type and classes of molecules such as those including a halide, an electron-donating group, an alkoxy group, amide group, amino group, an electron-withdrawing group, a nitro group, a carboxlic acid group, an ester group, a sulfoxide group, or a sulfone group, diazonium salts, electrophilic carbons, or a carbonyl group.

The large variations in reactivity of aromatic compounds with aryl diazonium salts may allow a significant degree of selectivity to be achieved in the analysis of mixtures of compounds. In a gross sense, aromatic analytes may be divided into electron rich and electron poor groups. Aromatic compounds more electron poor than benzine are not expected to react with Z—Ar—N2+, though exceptions may be possible. Electron rich analytes susceptible to analysis through diazonium based surface coatings include phenols, diaryl ethers, aryl alkyl ethers, aryl esters, aryl amines (anilines), aryl amides (ArNRCOR'), pyrroles, furans, thiophenes, and any other electron rich heteroaromatic ring system. For all of these compounds, the direct conjugation of the two aromatic rings through the diazo group may mean that adduct s could have very unique and distinguishable spectral signatures.

To further permit variation in the reactive functional groups end the analytes for controlled substances desired to be sensed, it is possible that the reactive functional group may be first presented as a reactive functional group precursor. In this fashion the group itself would not act at its initial configuration to achieve the reaction with the analyte but rather would require same type of activation step to convert it to its reactive form. Such may be presumed by subjecting the reactive functional group precursor to an activation substance. In this manner the reactive functional group precursor might be activated to produce a reactive functional group, namely, a substance which in its activated state would act to react with a desired analyte. Thus, the reactive functional group precursor might be activated to become the chemical reaction event location by being subjected to some type of activation substance. Examples of reactive functional group precursors include: but are not limited to aryl amines (for diazonium, RFGs), aryl amines or hydroxylamines or nitro groups (for nitroso RFGs), and carboxylic acids or alcohols or amines (for activated acyl groups RFGs). Examples of activation substances include: sodium nitrite, thionyl chloride, and the like as those skilled in the chemical arts would readily understand.

To permit even further variation, for certain classes of substrates, it may be possible to modify reactivity (and thus, selectivity in a sample containing mixed analyte classes) in either a positive or negative sense through manipulation of the reaction conditions. This strategy may be illustrated by considering a mixture of a phenol (ArOH), aryl ether (ArOR, R either aryl or alkyl) and an amine (ArNR2). At pH 7 all of these compounds are expected to be in neutral forms given above, and the better donor ability of nitrogen as compared to oxygen should result in a reactivity order of ArNR2>ArOH≈ArOR, allowing for selective/enhances detection of the aryl amine. At higher pH (>8–9), significant ionization of the phenol may generally take place to give phenolate, ArO—. Phenolate ions are among the most reactive species known towards diazonium salts, often showing near diffusion controlled rates of reaction. Thus, at conditions of high pH, the reactivity order is expected to be "ArOH">ArNR2>ArOr. Indeed, selectivity of this type has been seen in the case, of the reactions of 5-dimethylamino-1-naphthol with benzenediazonium ion. In this case, reaction occurs para to the dimethylamino group at low pH, and ortho to the oxygen at high pH. Finally, if exposure of a sensor coating were to take place at very low pH (e.g., pH≦3), the amino group of the arylamine would be in a protonated state (ArNR2H+), rendering the aromatic ring highly electron deficient and unreactive. Under these conditions the reactivity order should be ArOH=AOR>"ArNR2", allowing the assay of phenols and aryl ethers in the presence of the normally more reactive aryl amino.

It is possible that attachment of fine RFG and tether/SAG units to a central molecular scaffolding may result in a coating which reacts at a desirable rate with target analysis to give adducts having desirable characteristics from the standpoint of subsequent analysis. If these conditions am not met, however, it may be desirable to incorporate a modifier group, Z. The modifier (if employed) could be chosen so as to influence the reactivity of the RFG, although it may also play a role in enhancing the spectral characteristics of the adduct coating (e.g., in terms of λmax, extinction coefficient). In order to increase reactivity, it is likely that an electron withdrawing group would be chosen (e.g., nitro, carboxylic acid, ester, sulfoxide, sulfone). The nitro group illustrates the dual role which a modifier could play. In addition to increasing the reactivity of either a diazonium or activated acyl based sensor towards all analyte classes, the nitro group may appear particularly Raman active, suggesting its utility in a SERS bused detection system.

Thus, this arrangement could present a first modifier and a second modifier which could be attached to some aspect of the coating to achieve the desired result. In one regard the modifier might serve to reserve a position on the molecule to react with the controlled substance or the analyte involved. In another regard the modifier might serve to influence the reactivity between the reactive functional group and the analyte. This influence might actually serve to tune or influence the reaction to a desired degree. In one regard such tuning might serve to provide different ranges or concentrations at which the analyte reactive coating (8) would react. Thus, the sample (4) might be configured with a variety of sensor locations for each to serve as a sensor appropriate to a different range of concentrations. It should be noted in this regard that in other aspects of the invention multiple seniors can be essentially co-located at one sensor site to potentially achieve a similar type of capability. Regardless, the modifier might serve to create a group which could be adapted to influence the activity between the coating and the analyte to some desired degree. Interestingly, the modifier through its location on the reactive functional group or some other aspect can set different ranges based on the type of modifier chosen. Since these range variations can be many orders of magnitude different, a great degree of variation can be achieved through this embodiment of the present invention.

Figure 5:
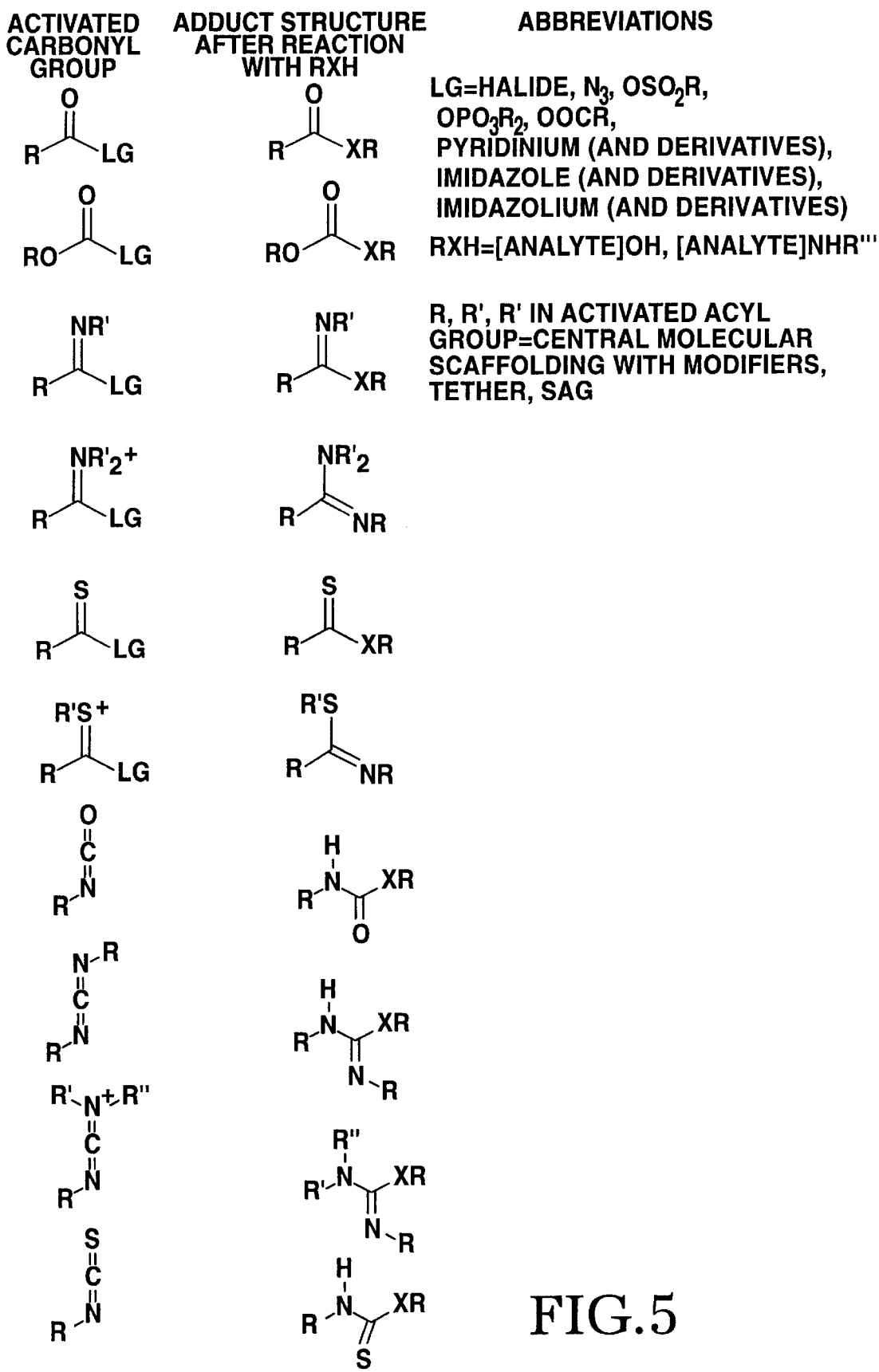
FIG. 5 shows some abbreviated chemical structures illustrating the types of acyl carbon derivatives which could be used as the RFG portion of a sensor molecule.

Examples of modifiers which may be utilized include electron donating group (oxygen or amine nitrogen or amide nitrogen), electron withdrawing groups (nitro, carboxylic acid, esters, sulfoxide and sulfones). As before, and as should be understood throughout this application, the examples should not be viewed as establishing a limitation to the invention. Under the basic teachings of the present invention those with ordinary skill in the chemical arts can easily vary the chemicals to achieve the desired result based upon the type of situation or type of analyte involved. Furthermore, a great degree of variations in the various substances involved is explained in FIG. 5. This teaching serves as a blueprint for the design of a great variety of chemicals according to the present invention.

As mentioned earlier, this invention has applicability in a variety of instances ranging from law enforcement to medical to environmental concerns. With the teachings of the present invention one need only understand the particular analyte involved and then utilize the teachings to attempt to design an appropriate reactive functional group or analyte-reactive coating (8) to achieve detection or analysts.

Without creating a limitation, some of the various analytes naturally include many controlled substances such as codeine, heroin, possibly cocaine, tetrahydrocannibinol (THC), morphine, amphetamines, methamphetamines, or the like. They also include a variety of other substances as discussed below. Analytes which should be well suited to detection by diazonium based sensor molecules include the following classes and types of substances.

Cyanide. Cyanide can react in a reversible fashion with Z—ArN$_2$+ to give Z—Ar—N=N—CN. It as of note that while this reaction is reversible, it involves the formation of an adduct which tumults from covalent band formation. This complex may be orange or red, depending on the geometry about the N=N double bond. There are two aspects of this reaction which may be of practical importance: its reversible nature, and the sensitivity of the reaction to the nature of Z. The reversible nature of this reaction means that it may be possible to construct a detection system which may be used multiple times (with appropriate intermediary rinses) and/or as a flow sensor to detect changing concentrations of cyanide in a waste stream. The sensitivity of the reaction to the nature of Z offers the possibility of making a detection system which is capable of quantifying cyanide concentration over a wide range of values. The Hammett equation for this reaction is log $(K_{CN})=3.53\sigma+182$, Thus, the equilibrium constant $K_{CN}$ for the reaction ranges from 60,000 M-1 for Z=p-NO$_2$ to 15 M$^{-1}$ for Z=p-CH$_3$. By employing mixtures of sensor molecule (each of which may have a unique spectrum), it may be possible to monitor a wide range at cyanide concentrations, since levels which may saturate (i.e., overload) a sensor molecule having Z=p-NO$_2$ typically may just be starting to effectively form adducts with a sensor molecule having Z=m-Cl (for which $K_{CN}$ is 1,600 M$^{-1}$). Since the spectra of differentially substituted adducts may be different, it generally will be possible to distinguish between them and determine their concentrations. It should be noted that some cyanide bonds—while covalent—may not be totally permanent, such adducts may not be appropriate for a washing procedure discussed earlier.

Sulphite. The sulfite ion undergoes very rapid reaction with aryl diazonium salts to give the syn isomer of the adduct Z—Ar—N=N—SO$_3$—. This intermediate may then undergo an isomerisation reaction to give the stable anti adduct, or under conditions of high sulfite concentration may add a second sulfite to give the bis-sulfite adduct Z—Ar—N(SO$_3$—)NHSO$_3$—. The rate of the syn-anti isomerization reaction is substantially slower than that of the initial adduct formation, with half-lives of about 250 sec and <2 sec, respectively. Furthermore, the rate of this isomerization is not greatly dependent on the identity of Z. With this relatively slow isomerization, it may be possible to directly measure sulfite concentrations by spectral assay immediately following exposure of the sensor coating to the analyte sample. However, by simply waiting for roughly 30 minutes (which is seven half-lives for the isomerization reaction), the isomerization reaction may be >99% complete, allowing concentrations to be measured from the spectrum of the anti mono-adduct. A further advantage of this approach may be that the secondary reaction of the syn- or anti-mono-adducts to give the bis-sulfite may provide a method by which higher concentrations of sulfite can be measured. Thus, molecules of this type may inherently be dual-range sensors.

Thiols. It may be possible to detect thiols and related species (e.g., xanthates) through the formation of adducts of the type Z—Ar—N=N—SR. The possible competing process of the binding of the thiol to the surface (for mental substrates) could be minimized by having a high level of surface coating density for the original sensor coating. In any case, should the thiol bind to the surface, it might be possible to detect its presence directly by spectroscopic means.

Sulfinic acids. Sulfinic acids react with Z—Ar—N$_2$+ to give Z—Ar—N=N—SO$_2$R, and thus should be amenable to detection by a diazonium based sensor coating. The extent of adduct formation, as well as the reversibility of adduct formation appears similar to that found with cyanide. Hence, such potentials for sensor coatings may be similar to those discussed for cyanide (e.g., reusable, applicable to flow systems, wide dynamic range through use of mixed coatings, etc.).

Amines. Ammonia and primary amines react with Z—Ar—N$_2$+ to give triazenes, Z—Az—N=N—NHR (R=H, alkyl, aryl amines are ultimately expected to lead to C—N coupled products, as discussed below for electron rich aromatic compounds). Alternatively, a use of a sensor coating having an oxidizing counterion (such as Br$_3$—) may lead to formation of aryl asides Z—Ar—N$_3$, with ammonia as the analyte. This distinction may allow primary amines to be analyzed in the presence ammonia by either direct observation and quantification of the final mixed adduct coating (Z—Ar—N=N—NHR and Z—Ar—N$_3$), or by sequential measurements with two different coatings (one with a non-oxidizing counterion, one with). Other derivative of amines which react with Z—Ar—N$_2$+ include hydrazines and hydroxylamine. Both of these types of compounds lead to azides and aryl amines. The fact that the reaction of hydroxylamine can be selectively directed by changes in reaction pH to give azides (low pH) or aryl amines (high pH) offers the possibility of distinguishing between the two classes of compounds.

Azide. The azide ion reacts extremely rapidly with Z—Ar—N$_2$+ to give Z—Ar—N$_3$. It thus could be spectroscopically sensed as mentioned above.

Carbon Acids. Compounds of the type RCH$_2$W, an which W is a strong electron withdrawing group (e.g., carbonyl, nitro, etc.) react with Z—Ar—N$_2$+ to form highly conjugated adducts of the type Z—Ar—NH—N=CRW. These reactions are known to proceed through the conjugate base of the analyte (i.e., RWCH—). Although this might be expected to mean that this detection method would be limited to strong carbon acids of the type WCH$_2$W', it appears that while the lower acidity of monoactivated carbon acids RCH$_3$W (R=H, alkyl, aryl) does indeed lead to lowered concentrations of the reactive conjugate base, there is a compensatory increase in reactivity of the base. Thus, even the relatively unacidic acetone has born observed to couple with benzenediazonium ions under nearly neutral conditions. For carbon acids having only a single acidic hydrogen, adducts of the form Z—Ar—N=N—CRR'W at expected to form. While the adducts lack a direct conjugative interaction with the sensor molecule, the —CRR'W group may still be attached in the vicinity of the surface, and may be susceptible to assay by certain spectroscopic techniques (e.g., SERS, reflectance FTIR) even if it lacks an appropriate chromophore for other techniques (e.g., fluorescence).

Electron Rich Aromatic Compounds. This class of compounds may prove to be the best suited class of analytes of all those discussed. The coupling of aromatic compounds Ar'—D (D=electron donating group) to aryl diazonium salts Z—Ar—N$_2$+ to give diazo compounds Z—Ar—N=N—Ar'D has been widely studied in the context of the production of dyes. The diazo adducts produced in these reactions absorb UV-Visible radiation strongly (i.e., have high extinction coefficients, $\epsilon$) and typically have their most intensely absorbing peak at high wavelengths (i.e., they have a $\lambda$max at high wavelengths), making them particularly well suited for detection by any of a number of spectroscopic techniques. These spectroscopic properties lend themselves particularly well to manipulation through judicious placement of modifier group(s) Z on Z—Ar—N$_2$+, and by variation of the molecular scaffolding Ar.

Other analytes in general may include phenolic compounds, furans, pyrroles, aryl amines, alcohols, and the like.

Yet another embodiment of the invention involves its teachings to create multiple sensors. In this regard coatings may be designed which present at least a first sensor molecule type and a second sensor molecule type. These molecule types would be differentiated in that each type would have its own reaction characteristics or its own differentiatable spectroscopic signal either with respect to the same analyte or with respect to different analytes. As such the first sensor molecule type could respond to a first type of analyte in one way to yield a first signal, and the second sensor molecule type could respond to a second type of analyte in another way to yield a second signal, etc. Naturally a plurality of molecule types could be utilized. In any such design the various sensor molecule types might be adapted to bond with different types of analytes, or, more generally, to somehow differently interact. They may even be adapted to interact differently with the same analyte and may, of course, each create their own adducts for spectroscopic analysis. These adducts would likely yield differentiatable spectroscopic signals in order to permit spectroscopic analysis to gain information about either one or multiple analytes.

In multiple sensor arrangements in which different analytes might be sensed, either the resulting adduct signal or the coating itself would likely be designed to yield a signal which would provide differentiating information between at least a first a second species of analyte. In this fashion, a single sensor could be utilized for multiple analytes simultaneously. It could also be used to provide conditional testing in which the presence of one in conjunction with another might yield some type of conclusion. Similarly, as mentioned earlier with regard to amine type analytes, sequential testing is also possible. Examples of this type of arrangement might include physically creating different sensors such as having one event location with a non-oxidizing counterion and another event location with an oxidizing counterion and the like, or might include separate sensor reaction protocols. Thus in one embodiment, the step of subjecting the analyte reactive coating (8) to an analyte may perhaps be specifically applied to a controlled substance or the like to yield multiple adduct types by creating each senor molecule type to achieve a different adduct result. The differentiated signals might not only yield information with respect to the mere presence of an analyte, but it also might serve for quantitating the presence of either or all of the various analytes sensed.

In a configuration where the same analyte might be sensed, it might be appropriate to configure the first and second sensor molecule types so that their interaction with the same analytes occurred in different concentration ranges or with some other different characteristics. In applications where different ranges of concentration were chosen, an enlarged range of sensitivity for the sample might be presented for a given analyte. These different ranges might be separate, such as in instances where discrete occurrences occurred or might more typically be established with awareness of the various saturation levels involved for the two different types of sensor molecules. In such as application where the first sensor molecule type had a first saturation level (that is, the level at which the changes in the signal can no longer be accurately discerned for variations in the analyte concentration or the like) and the second had a second saturation level which was higher than that of the first, it might be possible to use the first molecule up until it was near its saturation level and then to use the second sensor molecule type at a continued, expanded range. Furthermore, in instances in which an overlap region for the two sensor types might be present, it might be possible to provide verification of readings in this area via separate interaction mechanisms so that one could combine both an enlarged range and a verification of readings. In a more general sense, it would thus be possible to establish complementary ranges, namely, ranges (whether overlapping or not) which complimented each other for a given application to achieve a desired result (whether verification, expanded range, or otherwise). The first and second analytical ranges might not even be adjacent if the particular application called for such an arrangement. Furthermore, even though two different types of sensors might be provided on a specific coating it is now possible for these two sensors to provide capabilities, whether used or not, so that in practice one could sense for the presence of different controlled substances or the like with just one sensor plate.

In summary, some of the embodiments of the invasion include a surface coating comprising highly reactive sensor molecules which chemically react with a given analyte with the formation of a covalent and/or $\pi$-bond to give an adduct with spectroscopic characteristics which are unique to the new adduct. This surface coating may provide the basis of a detection system which combines high sensitivity with high specificity for the identification of certain analytes. The surface attachment of the sensor molecules allows reaction of the target analyte(s) to be followed by a rinse, which may remove nonreactive compounds which may possess interfering spectroscopic characteristics. This methodology contrasts radically from solution based analyte modification methods, in which non-target impurities may substantially decrease effective detector signal-to-noise ratios. The formation of a covalent bond (sigma or $\pi$) between the sensor molecule and the analyte to give a new, unique molecule (termed the adduct) greatly distinguishes this method from those in which hydrogen bonding, or other weak, or perhaps noncovalent interactions may serve to modify the spectral characteristics of a sensor molecule, or to bind the analyte in a location in which its spectral characteristics may be assayed. In one embodiment, the sensor molecules which comprise the coating may have three components attached to a central molecular scaffold: a "tether" terminated by a surface attachment group "SAG," a reactive functional group "RFG" which is highly reactive towards certain classes of molecules, and possibly one or more modifiers "Z" which may serve to increase or decrease the reactivity of the RFG towards target analytes, or to modify the spectral characteristics of the adduct in terms of either wavelength of maximum response to a given spectroscopic assay, or in terms of intensity of response to that assay. Variations in the nature of the tether may allow attachment to a variety of surfaces possessing desirable physical or spectroscopic characteristics. Variation of the RFG, and possibly the conditions under which the coating is exposed to the analyte containing solution, may allow detection selectivity for certain classes of analytes. Variations in the modifier group Z and the central molecular scaffold may significantly influence the nature and efficacy of the spectroscopic technique which is used to assay the premium of the adduct. Variations in these groups may also influence the reactivity of the sensor molecule.

The discussion included is this application is intended to serve as a basic description from which a great variety of systems can be fashioned. The reader should be aware that the specific discussion does not explicitly describe all embodiments possible; many alternatives are available through application of the teachings of this invention. It also may not fully explain the generic nature of the invention and may not explicitly show how each feature or element can actually be representative of a broader function or of a great variety of alternative or equivalent elements. Again, these are implicitly included in this patent disclosure. Neither the description, the examples, nor the terminology should be taken as an intention to limit the scope of this patent. Since a variety of changes may be made without departing from the essence of the invention, it should be understood that such changes are implicitly included within the scope of this invention.

In addition, each of the various elements of the invention and claims may also be achieved in a variety of manners. This disclosure should be understood to encompass each such variation, be it a variation of a embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, the disclosure of a "detection system" or "detector" should be understood to encompass disclosure of the act of "detecting"—whether explicitly discussed or not—and, conversely, were there only disclosure of the act of "detecting", such a disclosure should be understood to encompass disclosure of a "detector" or "detection system" (as the context may be appropriate). Similarly, surface "attachment" could include an "attachment element" or "attaching" and vice versa. Such changes and alternative terms are to be understood to be explicitly included in the description.

While the invention explains how to apply knowledge from the skills of persons in different disciplines, to facilitate this and to facilitate the creation of the many variations possible, a list of references is provided in an information disclosure filed with the application. All these are hereby incorporated by reference should they be needed. In any of these references, it should be understood that to the extent statements in any of the references might be considered inconsistent with the patenting of this invention such statements are expressly not to be considered as made by the applicant(s).

We claim:

1. A method for detection of a controlled substance, comprising the steps of:
   a) establishing a Raman spectroscopic sample surface;
   b) placing a diazonium compound sensor coating on said Raman spectroscopic sample surface;
   c) subjecting said diazonium compound sensor coating to a sample;
   d) retaining a diazonium-reactive controlled substance in said sample on said diazonium compound sensor coating on said Raman spectroscopic sample surface;
   e) exposing said diazonium-reactive controlled substance retained by said diazonium compound sensor coating on said Raman spectroscopic sample surface to radiation having at least one wavelength of energy;
   f) affecting a change in frequency of said at least one wavelength of energy at least in part by said diazonium-reactive controlled substance retained by said diazonium compound sensor coating on said Raman spectroscopic sample surface;
   g) detecting a Raman spectroscopic signal including said change in frequency of said at least one wavelength of energy; and
   h) analyzing said Raman spectroscopic signal to gain information about said diazonium-reactive controlled substance.

2. A method for detection of a controlled substance as described in claim 1 further comprising the step of affecting a change in amplitude of said at least one wavelength of energy at least in part by said diazonium-reactive controlled substance.

3. A method for detection of a controlled substance as described in claim 2 further comprising the step of detecting a Raman spectroscopic signal including said change in amplitude.

4. A method for detection of a controlled substance as described in claim 1, wherein said controlled substance is selected from the group consisting of codeine, heroin, psilocybin, tetrahydrocannabinol and morphine.

5. A method for detection of a controlled substance, comprising the steps of:
   a) establishing a Raman spectroscopic sample surface;
   b) placing an acyl compound sensor coating on said Raman spectroscopic sample surface;
   c) subjecting said acyl compound sensor coating to a sample;
   d) retaining a acyl-reactive controlled substance in said sample on said acyl compound sensor coating on said Raman spectroscopic sample surface;
   e) exposing said acyl-reactive controlled substance retained by said acyl compound sensor coating on said Raman spectroscopic sample surface to radiation having at least one wavelength of energy;
   f) affecting a change in frequency of said radiation having at least one wavelength of energy at least in part by said acyl-reactive controlled substance retained by said acyl compound sensor coating on said Raman spectroscopic sample surface;
   g) detecting a Raman spectroscopic signal including said change in frequency of said at least one wavelength of energy; and
   h) analyzing said Raman spectroscopic signal to gain information about said acyl-reactive controlled substance.

6. A method for detection of a controlled substance as described in claim 5 further comprising the step of affecting a change in amplitude of said at least one wavelength of energy at least in part by said acyl-reactive controlled substance.

7. A method for detection of a controlled substance as described in claim 6 further comprising the step of detecting a Raman spectroscopic signal including said change in amplitude.

8. A method for detection of a controlled substance as described in claim 5, wherein said acyl-reactive controlled substance is selected from the group consisting of codeine, heroin, tetrahydrocannabinol, morphine, psilocybin, amines, alcohols, amphetamines, and methamphetamines.

9. A method for detection of a controlled substance as described in claim 8, wherein said Raman spectroscopic sample surface comprises a Surface Enhanced Raman Scattering surface.

10. A method for detection of a controlled substance, comprising the steps of:
    a) establishing a Raman spectroscopic sample surface;
    b) placing a diazonium salt compound sensor coating on said Raman spectroscopic sample surface;
    c) subjecting said Raman spectroscopic sample surface to at least some diazonium-reactive controlled substance;

d) retaining a diazonium-reactive controlled substance on said diazonium salt compound sensor coating on said Raman spectroscopic sample surface;

e) exposing said diazonium-reactive controlled substance retained by said diazonium salt compound sensor coating on said Raman spectroscopic sample surface to radiation having at least one wavelength of energy;

f) affecting a change in frequency of said radiation having at least one wavelength of energy at least in part by said diazonium-reactive controlled substance retained by said diazonium salt compound sensor coating on said Raman spectroscopic sample surface;

g) detecting a Raman spectroscopic signal including said change in frequency of said at least one wavelength of energy; and h) analyzing said Raman spectroscopic signal to gain information about said diazonium-reactive controlled substance.

11. A method for detection of a controlled substance as described in claim 10 further comprising the step of affecting a change in amplitude of said at least one wavelength of energy at least in part by said diazonium-reactive controlled substance.

12. A method for detection of a controlled substance as described in claim 11 further comprising the step of detecting a Raman spectroscopic signal including said change in amplitude.

13. A method for detection of a controlled substance, comprising the steps of:

a) establishing a Raman spectroscopic sample surface;

b) placing a nitroso compound sensor coating on said Raman spectroscopic sample surface;

c) subjecting said nitroso compound sensor coating to a sample;

d) retaining a nitroso-reactive controlled substance in said sample on said nitroso compound sensor coating on said Raman spectroscopic sample surface;

e) exposing said nitroso-reactive controlled substance retained by said nitroso compound sensor coating on said Raman spectroscopic sample surface to radiation having at least one wavelength of energy;

f) affecting a change in frequency of said wavelength of energy at least in part by said nitroso-reactive controlled substance retained by said nitroso compound sensor coating on said Raman spectroscopic sample surface;

g) detecting a Raman spectroscopic signal including said change in frequency of said at least one wavelength of energy; and h) analyzing said Raman spectroscopic signal to gain information about said nitroso-reactive controlled substance.

14. A method for detection of a controlled substance as described in claim 13 further comprising the step of affecting a change in amplitude of said at least one wavelength of energy at least in part by said nitroso-relative controlled substance.

15. A method for detection of a controlled substance as described in claim 14 further comprising the step of detecting a Raman spectroscopic signal including said change in amplitude.

16. A method for detection of a controlled substance as described in claim 1, 5, 10, or 13, wherein said step of affecting a change in frequency of said at least one wavelength of energy comprises Raman scattering.

17. A method for detection of a controlled substance as described in claim 16, wherein said Raman scattering comprises Surface Enhanced Raman Scattering.

18. A method for detection of a controlled substance as described in claim 17, wherein said step of retaining a reactive controlled substance to a compound sensor coating comprises creating covalent bonds with said controlled substance over a period of time.

19. A method for detection of a controlled substance as described in claims 1, 5, 10 or 13 further comprising the step of washing said compound sensor coating on said Raman spectroscopic sample surface with a liquid.

20. A method for detection of a controlled substance as described in claim 19 wherein said step of washing said compound sensor coating on said spectroscopic sample surface with a liquid removes at least one interfering substance from said compound sensor coating on said spectroscopic sample surface.

21. A method for detection of a controlled substance as described in claim 19 wherein said step of washing said compound sensor coating on said spectroscopic sample surface with a liquid removes excess controlled substance from said compound sensor coating on said Raman spectroscopic sample surface.

22. A method for detection of a controlled substance as described in claims 1, 5, 10 or 13 further comprising the step of establishing a second compound sensor coating on said Raman spectroscopic sample surface.

23. A system for detection of a controlled substance, comprising:

a) a Raman spectroscope;

b) a Raman spectroscopic sample surface; and c) a diazonium compound sensor coating on said Raman spectroscopic sample surface, wherein said diazonium compound sensor coating retains diazonium-reactive substances in spectroscopic samples, and wherein said Raman spectroscope differentiates said diazonium-reactive controlled substances.

24. A system for detection of a controlled substance as described in claim 23 wherein said diazonium compound sensor coating on said Raman spectroscopic sample surface generates a covalent bond with said diazonium-reactive controlled substances.

25. A system for detection of a controlled substance as described in claim 23 and further comprising an adduct formed by said diazonium compound sensor coating on said spectroscopic sample surface and said chemical in said controlled substance.

26. A system for detection of a controlled substances, comprising:

a) a Raman spectroscope;

b) a Raman spectroscopic sample surface; and c) an acyl compound sensor coating on said Raman spectroscopic sample surface, wherein said acyl compound sensor coating retains acyl-reactive substances in spectroscopic samples, and wherein said Raman spectroscope differentiates said acyl-reactive controlled substances.

27. A system for detection of a controlled substance as described in claim 26 wherein said acyl compound sensor coating on said Raman spectroscopic sample surface generates a covalent bond with said controlled substances.

28. A system for detection of a controlled substance as described in claim 26 wherein said Raman surface comprises a Surface Enhanced Raman Scattering surface.

29. A system for detection of a controlled substance as described in claim 26 and further comprising a acyl activator to influence reactivity between said acyl compound sensor coating and said controlled substance.

30. A system for spectroscopic analysis of an analyte, comprising:
   a) a Raman spectroscopic sample surface, wherein said Raman spectroscopic surface comprises a Surface Enhanced Raman Scattering surface;
   b) at least one Raman spectroscopic sample location on said Raman spectroscopic surface; and
   c) a diazonium compound sensor coating at said at least one spectroscopic sample location; wherein said analyte comprises a diazonium-reactive analyte in a Raman spectroscopic sample, and wherein said diazonium compound sensor coating retains said diazonium-reactive analyte.

31. A system for spectroscopic analysis of an analyte as described in claim 30 wherein said diazonium compound sensor coating on said Raman spectroscopic sample surface establishes a covalent bond with said diazonium-reactive analyte.

32. A system for spectroscopic analysis of an analyte as described in claim 30 wherein said diazonium compound sensor coating on said Raman spectroscopic sample surface establishes a covalent bond with a chemical on said analyte.

33. A system for spectroscopic analysis of an analyte, comprising:
   a) Raman spectroscopic sample surface;
   b) at least one Raman spectroscopic sample location on said spectroscopic surface; and
   c) a nitroso compound sensor coating at said at least one spectroscopic sample location;
   wherein said analyte comprises nitroso-reactive analyte and wherein said nitroso compound sensor coating retains said nitroso-reactive analyte.

34. A system for spectroscopic analysis of an analyte as described in claim 33, wherein said Raman spectroscopic surface comprises a Surface Enhanced Raman Scattering surface.

35. A system for spectroscopic analysis of an analyte as described in claim 33 wherein said nitroso compound sensor coating on said spectroscopic sample surface establishes a covalent bond between said nitroso compound sensor coating and said nitroso-reactive analyte.

36. A system for spectroscopic analysis of an analyte, comprising:
   a) a Raman spectroscopic sample surface, wherein said Raman spectroscopic sample surface comprises a Surface Enhanced Raman Scattering surface;
   b) at least one spectroscopic sample location on said Raman spectroscopic surface; and
   c) an acyl compound sensor coating at said at least one spectroscopic sample location;
   wherein said analyte comprises an acyl-reactive analyte in a Raman spectroscopic sample, and
   wherein said acyl compound sensor coating retains said acyl-specific analyte.

37. A system for spectroscopic analysis of an analyte as described in claim 36 wherein said acyl compound sensor coating on said spectroscopic sample surface establishes a covalent bond with said acyl-reactive analyte.

38. A system for spectroscopic analysis of an analyte as described in claim 36 wherein said acyl compound sensor coating on said Raman spectroscopic sample surface establishes a covalent bond between said acyl compound sensor coating and an alcohol of said acyl-reactive analyte.

39. A system for spectroscopic analysis of an analyte as described in claims 30, 33 or 36, wherein said Raman spectroscopic sample surface further comprises a second compound sensor coating at said spectroscopic samples surface location.

40. A system for spectroscopic analysis of an analyte as described in claims 30, 33 or 36, wherein said compound sensor coating further comprises:
   a) a Raman spectroscopic sample surface covalent attachment group;
   b) a molecular scaffolding attached to said Raman spectroscopic sample surface attachment group; and
   c) a covalent bond between said molecular scaffolding and said compound sensor coating.

41. A system for spectroscopic analysis of an analyte as described in claims 30, 33, or 36, and further comprising:
   a) a Raman illumination device which illuminates said compound sensor coating on said Raman spectroscopic sample surface so as to produce a spectroscopic signal; and
   b) a sensor positioned so as to receive said spectroscopic signal.

42. A method of spectroscopic analysis of an analyte, comprising the steps of:
   a) establishing a Raman spectroscopic sample surface;
   b) placing an analyte-reactive coating on said spectroscopic sample surface;
   c) subjecting said analyte-reactive coating on said spectroscopic sample surface to a sample;
   d) covalently bonding analyte in said samples to said analyte-reactive coating on said Raman spectroscopic sample surface;
   e) exposing said analyte-reactive coating on said Raman spectroscopic sample surface to radiation having at least one wavelength of energy;
   f) affecting a change in frequency of said at least one wavelength of energy at least in part by said analyte covalently bonded to said analyte-reactive coating on said Raman spectroscopic sample surface; and
   g) analyzing said change in frequency of said at least one wavelength of energy to gain information about said analyte.

43. A method of spectroscopic analysis of an analyte as described in claim 42 further comprising the step of detecting a substantially unaltered signal.

44. A method of spectroscopic analysis of an analyte as described in claim 43 wherein said step of affecting a change in frequency of said at least one wavelength of energy at least in part by said analyte covalently bonded to said analyte-reactive coating on said Raman spectroscopic sample surface comprises Raman scattering.

45. A method of spectroscopic analysis of an analyte as described in claim 42 wherein said step of placing an analyte-reactive sensor coating on said spectroscopic sample surface:
   a) establishing a Raman spectroscopic sample surface covalent attachment group;
   b) establishing a molecular scaffolding to said Raman spectroscopic surface covalent attachment group; and
   c) establishing a covalent attachment between said molecular scaffolding and said analyte-reactive compound sensor coating.

46. A method of spectroscopic analysis of an analyte as described in claim 42 further comprising the step of washing said analyte-reactive compound coating on said Raman spectroscopic sample surface with a liquid.

47. A method of spectroscopic analysis of an analyte as described in claim 46 wherein said step of washing said analyte-reactive compound coating on said Raman spectroscopic sample surface with a liquid removes at least one interfering substance from said analyte-reactive compound coating on said Raman spectroscopic sample surface.

48. A method for detection of a controlled substance as described in claim 42 further comprising the step of affecting a change in amplitude of said at least one wavelength of energy at least in part by said analyte.

49. A method for detection of a controlled substance as described in claim 48 further comprising the step of analyzing said change in amplitude of said at least one wavelength of energy to gain information about said analyte.

50. A Raman spectroscopic sample surface, comprising:
   a) a Raman spectroscopic sample surface;
   b) an analyte-reactive coating on said Raman spectroscopic sample surface; and
   c) a chemical reactive event location on said analyte-reactive coating on said Raman spectroscopic sample surface to covalently bond an analyte to said analyte-reactive coating; and
   d) an internal standard, wherein said internal standard is co-located with said chemical reaction event location.

51. A system for spectroscopic analysis of an analyte as described in claim 50, further comprising:
   a) an illumination device which illuminates said chemical reaction event on said analyte-reactive coating on said Raman spectroscopic sample surface so as to produce a Raman spectroscopic signal; and
   b) a sensor positioned so as to receive said Raman spectroscopic signal.

52. A system for spectroscopic analysis of an analyte as described in claim 50 further comprising
   a) a Raman spectroscopic surface attachment group;
   b) a molecular scaffolding attached to said Raman spectroscopic surface attachment group; and
   c) a covalent bond between said molecular scaffolding and said analyte-reactive coating.

53. A system for spectroscopic analysis of an analyte as described in claim 52 wherein said analyte-reactive coating comprises
   a precursor reactive functional group attached to said central molecular scaffolding, wherein said precursor reactive functional group when activated becomes said chemical reaction event location.

54. A system for spectroscopic analysis of an analyte, comprising:
   a) a Raman spectroscopic sample surface;
   b) an analyte-reactive coating attached to said Raman spectroscopic sample surface comprising:
      1) a Raman spectroscopic sample surface attachment group;
      2) a central molecular scaffolding attached to said surface attachment group; and
      3) a reactive functional group attached to said central molecular scaffolding wherein said reactive functional group is adapted to react with an analyte to form a covalent bond; and
   c) an internal standard, wherein said internal standard is co-located with said chemical reaction event location.

55. A system for spectroscopic analysis of an analyte as described in claim 54 wherein said central molecular scaffolding attached to said surface attachment group is selected from the group consisting of a monocyclic aromatic ring, a polycyclic aromatic ring, a heteroaromatic ring, and a non-aromatic scaffolding.

56. A system for spectroscopic analysis of an analyte as described in claim 54 wherein said reactive functional group attached to said central molecular scaffolding is selected from the group consisting of a diazonium group, a diazonium salt, a nitroso, an activated acyl sensor, an electrophilic carbon, and a carbonyl.

57. A system for spectroscopic analysis of an analyte, comprising:
   a) a Raman spectroscopic sample surface;
   b) an analyte-reactive coating on said Raman spectroscopic sample surface, comprising:
      1) a Raman spectroscopic sample surface attachment group;
      2) a central molecular scaffolding attached to said surface attachment group; and
      3) a reactive functional group precursor attached to said central molecular scaffolding wherein said reactive functional group is adapted to be activated to become a reactive functional group attached to said central molecular scaffolding and wherein said reactive functional group attached to said central molecular scaffolding reacts with said analyte to form a covalent bond; and
   c) an internal standard, wherein said internal standard is co-located with said chemical reaction event location.

58. A system for spectroscopic analysis of an analyte as described in claim 57 further comprising an activation substance which activates said reactive functional group precursor to become said reactive functional group.

59. A system for spectroscopic analysis of an analyte as described in claim 58 wherein said reactive functional group precursor forms an adduct with said analyte after its activation by said activation substance.

60. A system for spectroscopic analysis of an analyte as described in claims 54 or 57 wherein said internal standard comprises a tether.

61. A system for spectroscopic analysis of an analyte as described in claims 54 or 57 wherein said surface attachment group and said central molecular scaffolding form at least part of a coating, and wherein said internal standard is selected from the group consisting of a non-carbon structure, a nitro group, a sulfonyl-group, a carbon structure, and a carbonyl group.

62. A method of spectroscopic analysis of an analyte, comprising the steps of:
   a) establishing a first sensor molecule type on a Raman spectroscopic sample surface;
   b) establishing a second sensor molecule type on said Raman spectroscopic sample surface;
   c) subjecting said spectroscopic sample surface to an analyte;
   d) covalently bonding said analyte to said first sensor molecule type;
   e) interacting said analyte with said second sensor molecule type;
   f) exposing said spectroscopic sample surface to radiation having at least one wavelength of energy;
   g) affecting a change in frequency of said at least one wavelength of energy at least in part by said analyte; and
   h) analyzing said change in frequency of said at least one wavelength of energy to gain information about said analyte.

63. A method of spectroscopic analysis of an analyte as described in claim 62 wherein said step of interacting said analyte with said second molecule type comprises the step of forming a covalent bond between said analyte and said second sensor molecule type.

64. A method of spectroscopic analysis of an analyte as described in claim 62 further comprising the step of affecting a change in amplitude of said at least one wavelength of energy at least in part by said analyte.

65. A method of spectroscopic analysis of an analyte as described in claim 64 further comprising the step of analyzing said change in amplitude of said at least one wavelength of energy to gain information about said analyte.

66. A method of spectroscopic analysis of an analyte, comprising the steps of:
   a) establishing a first sensor molecule type on a Raman spectroscopic sample surface;
   b) establishing a second sensor molecule type on said Raman spectroscopic sample surface;
   c) subjecting said Raman spectroscopic sample surface having said first sensor molecule type and said second sensor molecule type to samples at least a portion of which contain an analyte;
   d) interacting said analyte with said first sensor molecule type;
   e) interacting said analyte with said second sensor molecule type;
   f) exposing said spectroscopic sample surface to radiation having at least one wavelength of energy;
   g) affecting a change in frequency of said radiation having at least one wavelength of energy at least in part by said analyte bound to said first sensor molecule type or to said second sensor molecule type; and
   h) analyzing said change in frequency of said at least one wavelength of energy to gain information about said analyte.

67. A method of spectroscopic analysis of an analyte as described in claim 66 wherein said Raman spectroscopic sample surface comprises a Surface Enhanced Raman Scattering spectroscopic sample surface.

68. A method of spectroscopic analysis of an analyte as described in claim 66 further comprising the step of affecting a change in amplitude of said at least one wavelength of energy at least in part by said analyte bound to said first sensor molecule type or to said second sensor molecule type.

69. A method of spectroscopic analysis of an analyte as described in claim 68 further comprising the step of analyzing said change in amplitude of said at least one wavelength of energy to gain information about said analyte.

70. A method of spectroscopic analysis of an analyte, comprising the steps of:
   a) establishing a first sensor molecule type on a Raman spectroscopic sample surface which responds to a first concentration range of said analyte;
   b) establishing a second sensor molecule type on said Raman spectroscopic sample surface which responds to a second concentration range of said analyte wherein said first concentration range and said second concentration range are different;
   c) subjecting said Raman spectroscopic sample surface to an analyte;
   d) interacting said analyte with said first sensor molecule type;
   e) interacting said analyte with said second sensor molecule type;
   f) exposing said Raman spectroscopic sample surface to radiation having at least one wavelength of energy;
   g) affecting frequency of said radiation having at least one wavelength of energy at least in part by said analyte; and
   h) analyzing change in frequency of said radiation having at least one wavelength of energy to gain information about said analyte.

71. A method of spectroscopic analysis of an analyte as described in claim 70, wherein said first concentration range and said second concentration range have a concentration range overlap region created by said first sensor molecule type and said second sensor molecule type.

72. A method of spectroscopic analysis of an analyte as described in claim 71 wherein said first sensor molecule type has a first saturation level for said reactive analyte, wherein said second sensor molecule type has a second saturation level for said reactive analyte, and further comprising the step of establishing different saturation levels for said first sensor molecule type and said second sensor molecule type.

73. A method of spectroscopic analysis of an analyte as described in claim 72 wherein said step of establishing different saturation levels for said first sensor molecule type and said second sensor molecule types comprises the step of establishing complementary ranges provided by said first sensor molecule type and said second sensor molecule type.

74. A method of spectroscopic analysis of an analyte as described in claim 70 further comprising the step of affecting a change in amplitude of said at least one wavelength of energy at least in part by said analyte.

75. A method of spectroscopic analysis of an analyte as described in claim 74 further comprising the step of analyzing said change in amplitude of said at least one wavelength of energy to gain information about said analyte.

76. A method of spectroscopic analysis of an analyte as described in claim 62 or 70 and further comprising the steps of:
   a) establishing a first modifier attached to said first sensor molecule type on said spectroscopic sample surface; and
   b) establishing a second modifier attached to said second sensor molecule type on said spectroscopic sample surface.

77. A method of spectroscopic analysis of an analyte as described in claim 76 wherein said first modifier and a second modifier are selected from the group consisting of a halide, an electron-donating group, an alkoxy group, amide group, amino group, an electron-withdrawing group, a nitro group, a carboxylic acid group, an ester group, a sulfoxide group, and a sulfone.

78. A method for spectroscopic analysis of multiple species of analytes, comprising the steps of:
   a) establishing a first sensor molecule type on a Raman spectroscopic sample surface;
   b) establishing at least a second sensor molecule type on said Raman spectroscopic sample surface;
   c) subjecting said spectroscopic sample surface to at least a first species of analyte wherein said first species of analyte reacts with said first sensor molecule type on said spectroscopic sample surface;
   d) subjecting said Raman spectroscopic sample surface to at least a second species of analyte wherein said second species of analyte reacts with said second sensor molecule type on said spectroscopic sample surface;
   e) covalently bonding said first species of analyte to said first sensor molecule type;

f) interacting said second species of analyte with said second sensor molecule type;

g) exposing said Raman spectroscopic sample surface to radiation having at least one wavelength of energy;

h) affecting frequency of said radiation having at least one wavelength of energy at least in part by said first species of analyte;

i) affecting said frequency of radiation having at least one wavelength of energy at least in part by said second species of analyte; and j) simultaneously analyzing change in frequency of said radiation having at least one wavelength of energy due to said second species of analyte to gain information about said second species of said analyte.

79. A method for spectroscopic analysis of multiple species of analytes as described in claim 78 wherein said step of covalently bonding said first species of said analyte to said first sensor molecule type comprises the step of forming a first adduct type between said first species of said analyte and said first sensor molecule type.

80. A method for spectroscopic analysis of multiple species of analytes as described in claim 78 wherein said step of covalently bonding said first species of said analyte to said first sensor molecule type comprises the step of forming a first adduct type between said first species of said analyte and said first sensor molecule type, and wherein said step of interacting said second species of said analyte with said second sensor molecule type comprises the step of forming a second adduct type between said second species of said analyte and said second sensor molecule type.

81. A method for spectroscopic analysis of multiple species of analytes as described in claim 78 wherein said step of simultaneously analyzing said change in frequency of said radiation having at least one wavelength of energy to gain information about said second species of analyte comprises the step of differentiating information between said first species of analyte and said second species of said analyte.

82. A method for spectroscopic analysis of multiple species of analytes as described in claim 81 wherein said step of differentiating information between said first species of analyte and said second species of analyte comprises the step of quantitating said first species of analyte and quantitating said second species of analyte.

83. A method of spectroscopic analysis of an analyte as described in claims 78, 81, or 82 further comprising the step of affecting a change in amplitude of said at least one wavelength of energy at least in part by said second species of analyte.

84. A method of spectroscopic analysis of an analyte as described in claim 83 further comprising the step of analyzing said change in amplitude of said at least one wavelength of energy to gain information about said second species of analyte.

85. A system for spectroscopic analysis of an analyte, comprising:

a) Raman spectroscopic sample surface;

b) a first sensor molecule type on said Raman spectroscopic sample surface that forms a covalent bond with an analyte subjected to said Raman spectroscopic sample surface; and c) a second sensor molecule type on said Raman spectroscopic sample surface.

86. A system for spectroscopic analysis of an analyte as described in claim 85 wherein said second sensor molecule type forms a covalent bond between itself and said analyte subjected to said Raman spectroscopic sample surface.

87. A system for spectroscopic analysis of an analyte as described in claim 85 wherein said Raman spectroscopic sample surface comprises a Surface Enhanced Raman Scattering surface.

88. A system for spectroscopic analysis of an analyte, comprising:

a) a Raman spectroscopic sample surface;

b) a first sensor molecule type on said Raman spectroscopic sample surface which has a first concentration range for an analyte; and c) a second sensor molecule type on said Raman spectroscopic sample surface which has a second concentration range for said analyte wherein said first concentration range and said second concentration range are different.

89. A system for spectroscopic analysis of an analyte as described in claim 88 wherein said first concentration range and said second concentration range of said first sensor molecule type and said second sensor molecule type on said Raman spectroscopic sample surface have an overlap region.

90. A system for spectroscopic analysis of an analyte as described in claim 89 wherein said first sensor molecule type has a first saturation level for said analyte, and wherein said second sensor molecule type has a second saturation level for said analyte, and wherein said first saturation level and second saturation level are different.

91. A system for spectroscopic analysis of an analyte, comprising:

a) Raman spectroscopic sample surface;

b) a first sensor molecule type on said Raman spectroscopic sample surface which has a first analytical range; and c) a second sensor molecule type on said Raman spectroscopic sample surface which has a second analytical range, and wherein said first analytical range and said second analytical range are complementary.

92. A system for spectroscopic analysis of an analyte, comprising:

a) a Raman spectroscopic sample surface;

b) a first sensor molecule type on said Raman spectroscopic sample surface;

c) a first modifier attached to said first sensor molecule type that influences spectral characteristics of radiation having at least one wavelength;

d) a second sensor molecule type on said Raman spectroscopic sample surface; and e) a second modifier attached to said second sensor molecule type on said Raman spectroscopic sample surface.

93. A system for spectroscopic analysis of an analyte, comprising:

a) a Raman spectroscopic sample surface;

b) a first sensor molecule type on said Raman spectroscopic sample surface wherein said first sensor molecule type covalently bonds to a first type of analyte; and c) at least a second sensor molecule type on said Raman spectroscopic sample surface wherein said second sensor molecule type responds to a second type of analyte, and wherein said first type of analyte and said second type of analyte are different.

94. A system for spectroscopic analysis of an analyte as described in claim 93 wherein said first sensor molecule type on said Raman spectroscopic sample surface covalently bonds to said first type of analyte to form a first type of adduct for spectroscopic analysis.

95. A system for spectroscopic analysis of an analyte as described in claim 93 wherein said second sensor molecule type on said Raman spectroscopic sample surface covalently bonds to said second type of analyte to form a second type of adduct for spectroscopic analysis.

* * * * *